(12) United States Patent
Ohbayashi et al.

(10) Patent No.: US 7,940,398 B2
(45) Date of Patent: May 10, 2011

(54) OPTICAL COHERENCE TOMOGRAPHY APPARATUS

(75) Inventors: Kohji Ohbayashi, Kanagawa (JP);
Kimiya Shimizu, Kanagawa (JP)

(73) Assignee: School Juridical Person Kitasato Institute, Tokyo (JP)

( * ) Notice: Subject to any disclaimer, the term of this patent is extended or adjusted under 35 U.S.C. 154(b) by 0 days.

(21) Appl. No.: 12/502,670

(22) Filed: Jul. 14, 2009

(65) Prior Publication Data

US 2009/0279098 A1 Nov. 12, 2009

Related U.S. Application Data

(63) Continuation of application No. PCT/JP2007/050930, filed on Jan. 22, 2007.

(51) Int. Cl.
*G01B 9/02* (2006.01)

(52) U.S. Cl. ........................................................ 356/479

(58) Field of Classification Search .................. 356/479, 356/497
See application file for complete search history.

(56) References Cited

U.S. PATENT DOCUMENTS

| 5,444,528 A * | 8/1995 | Puschell | 356/73 |
| 5,892,583 A * | 4/1999 | Li | 356/479 |
| 6,501,551 B1 | 12/2002 | Tearney et al. | |
| 7,440,112 B2 | 10/2008 | Kurokawa et al. | |
| 2003/0055342 A1 | 3/2003 | Toida | |
| 2005/0018201 A1 | 1/2005 | De Boer et al. | |
| 2008/0018906 A1 | 1/2008 | Kurokawa et al. | |
| 2008/0024788 A1 | 1/2008 | Shimizu et al. | |
| 2008/0031410 A1 | 2/2008 | Shimizu et al. | |
| 2009/0002713 A1 | 1/2009 | Ohbayashi et al. | |

FOREIGN PATENT DOCUMENTS

| JP | A 2000-503237 | 3/2000 |
| JP | A 2003-90792 | 3/2003 |
| JP | A 2005-516187 | 6/2005 |
| JP | A 2006-184284 | 7/2006 |
| JP | A 2006-201087 | 8/2006 |
| WO | WO 2006/019181 A1 | 2/2006 |

OTHER PUBLICATIONS

S. H. Yun, et al., "High-speed spectral-domain optical coherence tomography at 1.3 μm wavelength," *Optics Express*, vol. 11, No. 26, pp. 3598-3604, Dec. 29, 2003.

(Continued)

*Primary Examiner* — Tarifur Chowdhury
*Assistant Examiner* — Jonathan D Cook
(74) *Attorney, Agent, or Firm* — Greer, Buns & Crain, Ltd.

(57) ABSTRACT

An optical coherence tomography apparatus constructs a tomographic image of a measurement object on the basis of a spectral characteristic obtained by spectrally dividing interference light, which combines signal light composed of the measurement light reflected by the measurement object and reference light, using an optical demultiplexer.

16 Claims, 14 Drawing Sheets

OTHER PUBLICATIONS

Takuji Amano, et al., "Optical frequency-domain reflectometry with a rapid wavelength-scanning superstructure-grating distributed Bragg reflector laser," *Applied Optics*, vol. 44, No. 5, pp. 808-816, Feb. 10, 2005.

S. H. Yun, et. al., "High-speed optical frequency-domain imaging," *Optics express*, vol. 11, No. 22, pp. 2953-2963, Nov. 3, 2003.

R. Huber, et al. "Fourier Domain Mode Locked Lasers for Swept Source OCT Imaging at up to 290 kHz Scan Rates," *Proc. of SPIE*, vol. 6079, pp. 60790U-1-60790U-6, 2006.

K. Okamoto, Amsterdam, "Fundamentals of Optical Waveguides," *Academic Press*, pp. 417-534, Dec. 2006.

Koh-ichi Aoyama, et al., "Low-loss optical demultiplexer for WDM systems in the 0.8- μm wavelength region," *Applied Optics*, vol. 18, No. 16, pp. 2834-2836, Aug. 15, 1979.

Duc Dung Do, et al., "Design of cascaded volume holographic gratings to increase the number of channels for an optical demultiplexer," *Applied Optics*, vol. 45, No. 34, pp. 8714-8721, Dec. 1, 2006.

Yuzo Yoshikuni, "Recent progress of tunable lasers for wavelength division multiplexing (WDM) systems," Oyo Buturi, vol. 71, No. 11, pp. 1362-1366, 2000.

* cited by examiner

OPTICAL FREQUENCY

WAVE NUMBER (OPTICAL FREQUENCY)

OPTICAL COHERENCE TOMOGRAPHY APPARATUS

CROSS-REFERENCE TO RELATED APPLICATIONS

This application is a continuation of international application PCT/JP2007/50930, filed on Jan. 22, 2007.

FIELD

The present invention relates to an optical coherence tomography apparatus, and more particularly to an optical coherence tomography apparatus using an optical demultiplexer, which has a high speed and a large depth range.

BACKGROUND

(1) Current State of OCT

Optical Coherence Tomography (OCT) is a high resolution optical tomography technique using an optical interference phenomenon. This technique is capable of realizing a high resolution (approximately 10 μm) close to the optical wavelength easily by employing the optical interference phenomenon. Furthermore, a probe used to capture a tomographic image is an optical probe, and therefore X-ray exposure does not pose a problem, in contrast to X-ray CT (Computed Tomography). Using these high resolution and non-invasive qualities, diagnosis apparatuses for observing the back of the eye and the anterior eye portion at a high resolution on a par with a microscope are realized through OCT.

Three OCT methods exist, namely TD-OCT, which is already in practical use, and SD-OCT and OFDR-OCT, which are still at the stage of research and development. TD-OCT is a time domain method, and was the first OCT method to be developed. SD-OCT is a spectral domain method, and has been under research for a comparatively long time (Japanese Laid-open Patent Publication No. 2006-184284.). OFDR-OCT is an optical frequency domain reflectometry method that has been developed recently (Japanese Laid-open Patent Publication No. 2006-201087.; T. Amano, H. Hiro-oka, D. Choi, H. Furukawa, F. Kano, M. Takeda, M. Nakanishi, K. Shimizu, and K. Ohbayashi, "Optical frequency-domain reflectormetry with a rapid wavelength-scanning superstructure-grating distributed Bragg reflector laser", *APPLIED OPTICS*, Vol. 44, p. 808-816, 2004.; S. H. Yun, G. J. Tearney, J. F. de Boer, N. Iftimia, and B. E. Bouma, "High-speed optical frequency-domian imaging", *OPTICS EXPRESS*, Vol. 11, p. 2953-2963, 2003.).

Incidentally, human tissue moves constantly in ways such as the flickering of the eye, the pulsation of blood vessels, and respiratory movement, for example, and is never stationary. Therefore, in OCT for capturing a tomographic image of tissue, it is important to capture moving images displaying a tomographic image in real time.

In TD-OCT, the apparatus constitution is simple, but there is an upper limit to the measuring speed, and therefore TD-OCT is not suitable for capturing a moving tomographic image. In contrast, SD-OCT and OFDR-OCT are capable of high speed measuring, and are therefore suitable for capturing a moving tomographic image. Further, the sensitivity (the reflectivity for forming signal power that is equal to the noise power) of SD-OCT and OFDR-OCT is between several ten and several thousand times higher than that of TD-OCT. Hence, the measurement range (the measurable depth) of SD-OCT and OFDR-OCT is greater than that of TD-OCT.

These high speed and high sensitivity qualities have been gaining attention, and in recent years, research into practical applications of SD-OCT and OFDR-OCT has been progressing rapidly.

SD-OCT uses a broadband light source such as a Super Luminescent Diode (SLD) as a light source (S. H. Yun, G. J. Tearney, B. E. Bouma, B. H. Park, and J. F. de Boer, "High-speed spectral-domain optical coherence tomography at 1.3 μm wavelength", *OPTICS EXPRESS*, Vol. 11, p. 3598-3604, 2003.). To construct a tomographic image, the output light of this broadband light source is divided, a measurement object (an object of measurement) is irradiated with divided first output light (measurement light), and the light reflected (or backscattered, to be referred to simply as "reflected" hereafter) by the measurement object is trapped and combined with divided second output light (reference light). Next, the resulting interference light is spectrally divided by a spectrometer, and the intensity of the interference light is measured at each wavelength.

By performing Fourier transform on the interference intensity at each wavelength relative to the wave number (=2π/wavelength), and doubling the absolute value thereof, the (depth direction) position in which the measurement light is reflected by the measurement object and the intensity of the reflection light are calculated.

The distribution of the reflection light intensity (to be referred to hereafter as the "reflectivity profile") is measured repeatedly at a large number of measurement points along a straight line on the surface of the measurement object, and a tomographic image is constructed on the basis of the results.

On the other hand, in OFDR-OCT, a narrow-band tunable wavelength light generating apparatus is used as a light source, and instead of spectrally dividing the interference light using a spectrometer, the intensity of interference light obtained by scanning the wave number of the output light of the light generating apparatus is measured for each wave number, and a tomographic image is constructed therefrom. This method was invented by the present inventors. In this method, a tunable wavelength semiconductor laser in which the wave number of the output light varies in steps (discretely) is used as a tunable wavelength light generating apparatus (T. Amano, H. Hiro-oka, D. Choi, H. Furukawa, F. Kano, M. Takeda, M. Nakanishi, K. Shimizu, and K. Ohbayashi, "Optical frequency-domain reflectormetry with a rapid wavelength-scanning superstructure-grating distributed Bragg reflector laser", *APPLIED OPTICS*, Vol. 44, p. 808-816, 2004).

Subsequently, OFDR-OCT using a variable wavelength laser known as a swept source was reported (S. H. Yun, G. J. Tearney, J. F. de Boer, N. Iftimia, and B. E. Bouma, "High-speed optical frequency-domian imaging", *OPTICS EXPRESS*, Vol. 11, p. 2953-2963, 2003.). A swept source is a type of fiber ring laser, and features a simple apparatus constitution. Further, a swept source differs from the tunable wavelength semiconductor laser used by the present inventors in that the wave number of the output light varies continuously. However, the two methods are substantially identical.

In both SD-OCT and OFDR-OCT, the intensity of the interference light is subjected to Fourier transform relative to the wave number. Accordingly, a technique including both SD-OCT and OFDR-OCT is occasionally referred to as FD-OCT (Frequency Domain OCT).

Note that OCT is a new technology, and therefore the names of the three types of OCT described above are not universal. As the employed names differ from document to document, care should be taken when referring to these documents.

(2) Constitution of SD-OCT apparatus (S. H. Yun, G. J. Tearney, B. E. Bouma, B. H. Park, and J. F. de Boer, "High-speed spectral-domain optical coherence tomography at 1.3 μm wavelength", *OPTICS EXPRESS*, Vol. 11, p. 3598-3604, 2003.).

Next, the principles and apparatus constitution of SD-OCT will be described briefly. FIG. 13 shows the constitution of an SD-OCT apparatus. Note that in the drawings to be described below, parts having identical functions have been allocated identical reference numerals.

As shown in FIG. 13, SD-OCT uses a broadband light generating device 1 such as a super luminescent diode (SLD). A light output port of the broadband light generating device 1 is optically connected to a light input port 21 of an optical circulator 2. Note that in FIG. 13, optical connections between each optical member are realized by optical fibers indicated by solid lines (hereafter, the term "optically connected" indicates that optical members are connected by optical fiber).

A light-output and light-input port 22 of the optical circulator 2 is connected to a first light-output and light-input port 31 of an optical-divider and optical-coupler 3 composed of a directional coupler for dividing light into two (at 10:90, for example).

A second light-output and light-input port 32 (on the 90% divided proportion side) of the optical-divider and optical-coupler 3 is connected to a light-irradiating and light-trapping unit 6 for irradiating a measurement object 5 with measurement light and trapping signal light reflected by the measurement object 5.

Note that the term "measurement light" denotes the light that is emitted onto the measurement object 5, from the output light of the broadband light generating device 1, which is divided by the coupler 3. The rest of the output light of the broadband light generating device 1 (on the 10% side), which is divided by the optical-divider and optical-coupler 3, is referred to as reference light. The light that is obtained when the measurement light is reflected by the measurement object 5 and trapped in the light-irradiating and light-trapping unit 6 again is referred to as signal light.

The light-irradiating and light-trapping unit 6 includes a collimator lens 7 for shaping the measurement light that is divided by the coupler 3 into parallel beams, a focusing lens 8 for converging the parallel beams into the measurement object 5, and a galvanometer mirror 9 for scanning the surface of the measurement object 5 with the measurement light in a linear fashion by deflecting the measurement light.

A third light-output and light-input port 33 (on the 10% divided proportion side) of the optical-divider and optical-coupler 3 is optically connected to an optical delay device 11 for delaying the reference light outputted from an optical fiber end portion 10 by causing the reference light to go from the optical fiber end portion 10 to a reference mirror 4 and back. The reference mirror 4 is supported by a support so as to be capable of moving forward and backward, and the position thereof is adjusted such that the optical path lengths of a reference arm 12 and that of a sample arm 13 are substantially equal.

A light output port 23 of the optical circulator 2 is optically connected to a light input port 41 of a spectrometer 14. In the interior of the spectrometer 14, a Diffraction Grating (DG) 15 disperses incident light. The incident light dispersed by the diffraction grating 15 is imaged onto an InGaAs CCD array scan camera 17 by an achromatic doublet lens 16.

An output of the InGaAs CCD array scan camera 17 is electrically connected to a computing and control apparatus 19, namely a computer, via a data acquisition board 18 composed of an analog-digital converter. An output portion of the computing and control apparatus 19 is electrically connected to an input portion of a display apparatus (not shown) such as a monitor or printer for displaying calculation results. The computing and control apparatus 19 controls the broadband light generating device 1 and the galvanometer mirror 9 of the light-irradiating and light-trapping unit 6 on the basis of input information.

A tomographic image is constructed in the following manner. The output light of the broadband light generating device 1 enters a Michelson interferometer includes the optical-divider and optical-coupler 3, the reference arm 12, and the sample arm 13, whereupon the signal light reflected by the measurement object 5 and the reference light reflected by the reference mirror 4 interfere in the optical-divider and optical-coupler 3. The interference light is spectrally divided by the diffraction grating 15, and the spectrum of the interference light is converted into an electric signal by the InGaAs CCD array scan camera 17. This electric signal is encoded by the data acquisition board and inputted into the computing and control apparatus 19.

The computing and control apparatus 19 constructs the spectrum of the interference light on the basis of input data. The computing and control apparatus 19 subjects the constructed spectrum to Fourier transform relative to the wave number, and calculates the squared absolute value thereof. The squared absolute value of the Fourier transform obtained in this manner is a function of the position, where the measurement light is reflected by the measurement object 5, and the intensity of the resulting reflection light.

In other words, the depth direction distribution of the reflectivity relating to the measurement object (more precisely, the reflectivity profile relative to the irradiation direction of the measurement light) is obtained. The measurement that is performed to obtain the depth direction distribution of the reflectivity relating to the measurement object is referred to as an A-line scan.

Next, the computing and control apparatus 19 issues a command to the galvanometer mirror 9 to move the measurement light irradiation position gradually along a straight line on the surface of the measurement object 5, and repeats the reflectivity profile measurement (A-line scan) described above. Finally, the obtained reflectivity profiles are amalgamated to construct a tomographic image of the measurement object 5.

(3) Constitution of OFDR-OCT apparatus (T. Amano, H. Hiro-oka, D. Choi, H. Furukawa, F. Kano, M. Takeda, M. Nakanishi, K. Shimizu, and K. Ohbayashi, "Optical frequency-domain reflectormetry with a rapid wavelength-scanning superstructure-grating distributed Bragg reflector laser", *APPLIED OPTICS*, Vol. 44, p. 808-816, 2004.)

Next, the principles and apparatus constitution of OFDR-OCT will be described briefly.

FIG. 14 shows the apparatus constitution of OFDR-OCT.

As shown in FIG. 14, an OFDR-OCT apparatus has a light output port of a tunable wavelength light generating apparatus 51 such as a super-structure grating distributed Bragg reflector laser (SSG-DBR laser) light generating apparatus (Yuzo YOSHIKUNI, "Recent progress of tunable lasers for wavelength division multiplexing systems", *OYO BUTURIT*, Japan Society of Applied Physics, 2002, Vol. 71, No. 11, p. 1362-1366.), which is capable of outputting light while changing the wavelength thereof. The light output port of the tunable wavelength light generating apparatus 51 is optically connected to a light input port of a first coupler 52 (optical divider) composed of a directional coupler for dividing light into two (at 10:90, for example).

Incidentally, a coupler composed of a directional coupler functions as both an optical divider and an optical coupler. In the SD-OCT apparatus shown in FIG. 13, the directional coupler functions simultaneously as both an optical divider and an optical coupler. In the OFDR-OCT apparatus shown in FIG. 14, however, the coupler composed of a directional coupler functions as only one of an optical divider and an optical coupler. Hence, in the OFDR-OCT apparatus shown in FIG. 14, a light input port and a light output port can be defined for the couplers 52, 54.

A first light output port (on the 90% divided proportion side) of the first coupler 52 is optically connected to the light input port 21 of a first optical circulator 53. The light-output and light-input port 22 of the optical circulator 53 is connected to the light-irradiating and light-trapping unit 6 for irradiating the measurement object 5 with measurement light and trapping the signal light that is reflected by the measurement object 5. The light output port 23 of the optical circulator 53 is connected to a first light input port of a second coupler 54 (optical coupler) composed of a directional coupler (with a division ratio of 50:50).

Note that the term "measurement light" denotes the light that is emitted onto the measurement object 5, from the output light of the tunable wavelength light generating apparatus 51, which is divided by the first coupler 52. The rest of the output light of the tunable wavelength light generating apparatus 51, which is divided by the first coupler 52, is referred to as reference light. The light that is obtained when the measurement light is reflected by the measurement object 5 and re-enters an interferometer (a Mach-Zehnder interferometer including the first and second couplers 52, 54 and the first and second circulators 53, 55) is referred to as signal light.

The light-irradiating and light-trapping unit 6 includes the collimator lens 7 for shaping the measurement light outputted from the light-output and light-input port of the optical circulator 53 into parallel beams, the focusing lens 8 for converging the parallel beams into the measurement object 5, and the galvanometer mirror 9 for scanning the surface of the measurement object 5 with the measurement light in a linear fashion by deflecting the measurement light.

A second light output port (on the 10% divided proportion side) of the first coupler 52 is optically connected to the light input port 21 of an optical circulator 55. The light-output and light-input port 22 of the first optical circulator 55 is optically connected to the optical delay device 11 for delaying the reference light outputted from an optical fiber end portion by causing the reference light to go from the optical fiber end portion to the reference mirror 4. The reference mirror 4 is supported by a support so as to be capable of moving forward and backward, and the position thereof is adjusted such that the optical path lengths of a reference arm 12 and a sample arm 13 are substantially equal.

The light output port 23 of the optical circulator 55 is optically connected to a second light input port of the second coupler 54 composed of a directional coupler (with a division ratio of 50:50). The first and second light output ports of the second coupler 54 are optically connected to first and second photodetectors 60, 61 having identical quantum efficiencies. Outputs of the first and second photodetectors 60, 61 are electrically connected to a differential amplifier 62.

An output portion of the differential amplifier 62 is electrically connected to an input portion of the computing and control apparatus 19, which synthesizes the reflectivity profile, or in other words the reflectivity distribution, via an analog-digital converter, not shown in the drawing. An output portion of the computing and control apparatus 19 is electrically connected to an input portion of a display apparatus (not shown) such as a monitor or printer for displaying calculation results. The computing and control apparatus 19 controls the tunable wavelength light generating apparatus 51 and the galvanometer mirror 9 of the light-irradiating and light-trapping unit 6 on the basis of input information.

A tomographic image is constructed in the following manner.

Laser light, or in other words narrowband light, is outputted from the tunable wavelength light generating apparatus 51 while changing the wave number ($=2\pi$/wavelength) thereof one after another in an extremely narrow wave number spacing. The output light of the tunable wavelength light generating apparatus 51 enters the interferometer (Mach-Zehnder interferometer) including the first and second couplers 52, 54 and the first and second circulators 53, 55, whereupon the signal light reflected by the measurement object 5 and the reference light reflected by the reference mirror 4 interfere in the second coupler 54. The intensity of the interference light is detected by the first and second photodetectors 60, 61, whereupon a direct current component (proportional to the sum total of the reference light intensity and the signal light intensity) of the interference light is removed by the differential amplifier 62, so that only an interference component (to be referred to hereafter as the amplitude of the interference light intensity) is inputted into the computing and control apparatus 19. The computing and control apparatus 19 records the wave number of the laser light outputted by the tunable wavelength light generating apparatus 51 and the output of the differential amplifier 62 relative to the laser light (to be referred to as the signal intensity hereafter) in relation to all wave numbers.

When the wave number scan of the tunable wavelength light generating apparatus 51 is complete, the computing and control apparatus 19 subjects the recorded signal intensity to Fourier transform relative to the wave number, and calculates the squared absolute value thereof. The result obtained in this manner is a function of the position, where the measurement light is reflected by the measurement object 5, and the intensity of the resulting reflection light. In other words, the depth direction distribution of the reflectivity relating to the measurement object (more precisely, the reflectivity profile relative to the irradiation direction of the measurement light) is obtained.

Note that in a wave number scan, the tunable wavelength light generating apparatus gradually varies the wave number of the output light (relative to time) from one end to the other end of the tunable wavelength band thereof. The wave number change may be continuous or stepped (discrete).

Next, the computing and control apparatus 19 moves the measurement light irradiation position gradually along a straight line on the surface of the measurement object 5, and repeats the reflectivity profile measurement (A-line scan). Finally, the obtained reflectivity profiles are amalgamated to construct a tomographic image of the measurement object 5. The measurement light irradiation position is moved by the light-irradiating and light-trapping unit 6 on the basis of a command from the computing and control apparatus 19 (Japanese Unexamined Patent Application Publication 2006-184284).

SUMMARY

As described above, SD-OCT and OFDR-OCT (i.e. FD-OCT) feature high-speed and high sensitivity. However, the conventional performance of FD-OCT is insufficient for realizing advanced diagnoses on a larger variety of body parts.

For various reasons, such as pulsation, living tissue moves constantly. Hence, by making it possible to capture a moving tomographic image, the range of OCT diagnosis subjects can be expanded to rapidly moving body parts. In other words, if it is possible to capture a moving tomographic image, a larger number of body parts can be diagnosed.

Meanwhile, when a large amount of information relating to human tissue is gathered in an attempt to perform an advanced diagnosis, a three-dimensional image is required.

Therefore, a three-dimensional moving image should be captured to realize an advanced diagnosis through OCT on a large number of body parts, including rapidly moving tissue.

The speed with which a tomographic image is captured using FD-OCT is much faster than that of TD-OCT. Therefore, the imaging speed of FD-OCT is sufficient to capture a (two-dimensional) moving tomographic image. However, the imaging speed of FD-OCT is not sufficient to capture a three-dimensional moving image. To capture a three-dimensional moving image, the measurement speed of FD-OCT should be improved by approximately two digits. However, it is impossible to realize such a measurement speed improvement with conventional FD-OCT.

It is therefore a first object of the present invention to provide a novel OCT technique having a measurement speed which is greater than that of conventional FD-OCT by at least two digits.

In terms of the high sensitivity characteristic, with FD-OCT, human tissue can be observed more deeply. However, the depth range (measurable range) is at most between 2 and 3 mm from the surface of the measurement object. With this depth range, the diagnosis subject is limited to body parts made of extremely thin tissue (the retina, for example).

In other words, to expand the variety of OCT subjects, it is important to increase not only the measurement speed, but also the depth range. It is therefore a second object of the present invention to provide a novel OCT technique having a greater depth range than that of conventional FD-OCT.

In other words, an object of the present invention is to provide a novel OCT technique having a measurement speed which is greater than that of conventional FD-OCT by at least two digits and a greater depth range than that of conventional FD-OCT.

The first and second objects will now be described in further detail.

(1) Improving FD-OCT Measurement Speed (First Object)

First, the need to improve the OCT measurement speed and factors limiting the FD-OCT measurement speed will be described.

(i) Need to Improve Measurement Speed

The number of times an A-line scan is repeated in one second is known as the A-line scan rate ($f_A$). The OCT measurement speed is evaluated according to the A-line scan rate ($f_A$).

To capture a clear tomographic image that is unaffected by the movement of bodily organs such as flickering of the eye, peristalsis of the bowels, and beating of the heart, an A-line scan rate between several kHz and several tens of kHz is required.

For example, to capture a tomographic image of the eye that is unaffected by flickering of the eye, an A-line scan rate of several kHz or more is required. Meanwhile, to capture a tomographic image of the heart or a blood vessel that is unaffected by heartbeat, an A-line scan rate of several tens of kHz or more is required.

Incidentally, a frequency between 20 and 30 kHz has been reported as the A-line scan rate of SD-OCT (S. H. Yun, G. J. Tearney, B. E. Bouma, B. H. Park, and J. F. de Boer, "High-speed spectral-domain optical coherence tomography at 1.3 µm wavelength", OPTICS EXPRESS, Vol. 11, p. 3598-3604, 2003.). This A-line scan rate is sufficient to capture a (two-dimensional) moving tomographic image.

To construct a three-dimensional image, several hundred tomographic images should be captured while a tomographic image (two-dimensional image) capturing position is moving gradually in a direction perpendicular to the tomographic image. Accordingly, to construct a three-dimensional moving image, the A-line scan rate should be increased by 100 times or more beyond the rate required to capture a (two-dimensional) moving tomographic image.

The maximum value of the A-line scan rate in an A-line scan executed in reality to capture a tomographic image is 58 kHz, which was achieved during OFDR-OCT using a swept source (R. Huber, K. Taira, M. Wojtkowski, and J. G. Fujimoto, "Fourier Domain Mode Locked Laser for Swept Source OCT Imaging at up to 290 kHz Scan Rates", Proc. of SPIE, Vol. 6079, pp. 60790U-1 60790U-6 (2006)). An investigation will now be conducted into whether it is possible to capture a three-dimensional moving image at this A-line scan rate.

Note that a high frequency of 290 kHz has been reported as the wave number repetition frequency of a swept source. However, the repetition frequency at which tomographic image capturing is successful, or in other words the maximum value of the A-line scan rate, is 58 kHz (R. Huber, K. Taira, M. Wojtkowski, and J. G. Fujimoto, "Fourier Domain Mode Locked Laser for Swept Source OCT Imaging at up to 290 kHz Scan Rates", Proc. of SPIE, Vol. 6079, pp. 60790U-1 60790U-6 (2006)).

To capture a three-dimensional image, first an A-line scan is repeated 256 times along a straight line on the surface of the measurement object, whereby a single tomographic image (a frame) is captured. Next, tomographic image capturing is repeated 256 times while the imaging position is moving little by little in a direction perpendicular to the straight line (to be referred to as a perpendicular direction hereafter). Finally, the obtained tomographic images (two-dimensional images) are arranged into a three-dimensional image.

In this case, an imaging time of 1.13 seconds (=(1/58,000 Hz)×256×256) is required to obtain all of the data required to construct a three-dimensional image.

It is difficult for a bodily organ to remain stationary even for this short amount of time. Hence, while the data required to construct the three-dimensional image are obtained, the imaging subject body part moves. As a result, deviation occurs between the frames when the captured frames are lined up one by one in the perpendicular direction to construct a three-dimensional image, and the resulting three-dimensional image is strikingly warped.

To capture a three-dimensional image that is unaffected by the movement of the bodily organ, the three-dimensional image capturing time should be approximately the same as the time required to capture a two-dimensional image using conventional FD-OCT. In other words, the measurement speed should be greater than the measurement speed of conventional FD-OCT by a multiple corresponding to the number of frames required to construct the three-dimensional image.

Accordingly, to capture a three-dimensional image, the measurement speed should be several hundred times (in the above example, 256 times) faster than that of conventional FD-OCT.

(ii) Factors Limiting Measurement Speed

In an A-line scan performed during SD-OCT, the interference light generated in the optical-divider and optical-coupler 3 is spectrally divided and then projected onto a one-dimensional line sensor (the InGaAs CCD array scan camera 17 shown in FIG. 13) having a large number of detector pixels (light detection elements) as a continuous spectrum. Each detector pixel (to be referred to as a pixel hereafter) of the one-dimensional line sensor stores a charge generated by the respective InGaAs photodetectors for a fixed time period, whereupon the charges stored in the respective detector pixels are read using the CCD in sequence. The time required to store and read the charges limits the SD-OCT measurement speed.

In other words, the SD-OCT measurement speed is limited by the operating speed of the InGaAs CCD array scan camera 17. However, the operating speed of the InGaAs CCD array scan camera 17 is unlikely to increase dramatically in the future, and therefore it is considered difficult to achieve further improvements in the A-line scan rate.

Meanwhile, the A-line scan rate of OFDR-OCT is limited by the speed at which the tunable wavelength light generating apparatus scans the wave number of the output light. The highest frequency value reported in the related art as the A-line scan rate of OFDR-OCT is 58 kHz. This frequency is limited by the operating speed of a tunable wavelength filter constituting the tunable wavelength light generating apparatus. However, the operating speed of the tunable wavelength filter is unlikely to increase dramatically, and it is therefore considered difficult to achieve further improvements in the A-line scan rate of OFDR-OCT.

Hence, the upper limit of the measurement speed of conventional FD-OCT (SD-OCT and OFDR-OCT) is believed to be several tens of Hz, and it is therefore considered difficult to capture a three-dimensional moving tomographic image of living tissue using conventional FD-OCT.

(2) Enlargement of FD-OCT Depth Range (Second Object)

Next, the need for an improvement in the OCT depth range and factors limiting the FD-OCT depth range will be described.

(i) Need for Enlargement of Depth Range

The depth range of FD-OCT is approximately 2.0 mm in SD-OCT and approximately 2.5 mm in OFDR-OCT (S. H. Yun, G. J. Tearney, B. E. Bouma, B. H. Park, and J. F. de Boer, "High-speed spectral-domain optical coherence tomography at 1.3 µm wavelength", *OPTICS EXPRESS*, Vol. 11, p. 3598-3604, 2003.; S. H. Yun, G. J. Tearney, J. F. de Boer, N. Iftimia, and B. E. Bouma, "High-speed optical frequency-domian imaging", *OPTICS EXPRESS*, Vol. 11, p. 2953-2963, 2003.). This depth range is sufficient to measure the retina. However, with this depth range, it is difficult to capture a tomographic image of the bowels, whose surface is contoured in a complicated manner. To capture a tomographic image of the bowels, a minimum depth range of approximately 5 mm is needed.

Hence, to expand the range of application of OCT to the diagnosis of tissue other than the retina, it is necessary to increase not only the measurement speed, but also the depth range (in other words, the measurable range).

In OFDR-OCT, however, the signal intensity decreases as the measurement position deepens, as will be described below, and ultimately, the signal becomes buried in noise. Therefore, the depth range is limited to 2 to 3 mm.

In other words, to increase the number of body parts that can be subjected to OCT diagnosis, the FD-OCT depth range of 2 to 3 mm should be increased.

(ii) Factors Limiting SD-OCT Depth Range

Factors limiting the depth range differ between SD-OCT and OFDR-OCT. First, the reason why the signal intensity decreases in deep positions will be described with respect to SD-OCT.

To simplify the description, it is assumed that the measurement object is constituted by a single mirror. In this case, there is a single light reflection surface, and the OCT signal serves as a function having a single peak relative to a coordinate z in the depth direction (the starting point being the point at which the optical path length of the reference arm is equal to that of sample arm).

A relative intensity $R(z_0)$ of the OCT signal (i.e. the reflectivity) at the single peak is expressed by the following equation in relation to a mirror position $z_0$ (S. H. Yun, G. J. Tearney, B. E. Bouma, B. H. Park, and J. F. de Boer, "High-speed spectral-domain optical coherence tomography at 1.3 µm wavelength", *OPTICS EXPRESS*, Vol. 11, p. 3598-3604, 2003.). Note that $R(z_0)$ is the relative intensity.

$$R(z_0) = \left(\frac{\sin\varsigma}{\varsigma}\right)^2 \cdot \exp\left[-\frac{w^2}{2\ln 2}\varsigma^2\right] \quad (1)$$

Here, $$\varsigma = \left(\frac{\pi}{2}\right) \cdot \left(\frac{z_0}{z_{RD}}\right) \quad (2)$$

$$z_{RD} = \frac{\pi}{2\Delta k} \quad (3)$$

$$w = \frac{\delta k}{\Delta k} \quad (4)$$

Here, $z_{RD}$ is the upper depth range limit according to the measurement principles, or in other words a maximum ranging depth. As shown in Equation (3), $z_{RD}$ is determined by a spacing $\Delta k$ (more precisely, a center wavelength spacing) of a wave number $k$ ($=2\pi/\lambda$, where $\lambda$ is the wavelength) of the light received by each pixel of the array scan camera.

Meanwhile, $\delta k$ is the resolution (FWHM) of a spectroscopy unit composed of the collimator lens, the diffraction grating 15, and the achromatic doublet lens 16.

Note that when the pixel spacing of the array scan camera or the resolution of the spectroscopy unit is expressed by the wavelength spacing $\Delta\lambda$ and the wavelength resolution $\delta\lambda$, the pixel spacing of the array scan camera or the resolution of the spectroscopy unit should be converted into $\Delta k$ and $\delta k$ and then inserted into Equation (1).

The right side of Equation (1) is divided into two items. The following equation is the front half part of the right side of Equation (1).

This function decreases monochromatically while $z_0$ is between 0 and $z_{RD}$.

$$\left(\frac{\sin\varsigma}{\varsigma}\right)^2 \quad (5)$$

The value of Equation (5) at the maximum ranging depth ($z_{RD}$) is 0.41 (−3.9 dB).

In other words, the relative value $R(z_0)$ of the OCT signal decreases by −3.9 dB in the maximum ranging depth ($z_{RD}$) in accordance with the contribution of Equation (5). This decrease is due to the fact that when z increases, a fringe formed on the one-dimensional line sensor by the diffraction grating 15 starts to oscillate in a small period.

An optical intensity density $I^*_c(k)$ of the interference light that is emitted onto the one-dimensional line sensor of the array scan camera may be expressed as follows.

$$I^*_c(k)=I^*_r+I^*_s+2\sqrt{rI^*_rI^*_o}\cos(2kz_0+\phi) \quad (6)$$

Note that $I^*_c(k)$ is the optical intensity of the interference light per unit wave number (to be referred to hereafter as the "optical intensity density").

Further, $I^*_r$ is the optical intensity density of the reference light, $I^*_o$ is the optical intensity density of the measurement light, and $I^*_s$ is the optical intensity density of the signal light. Here, $I^*_r$, $I^*_o$, and $I^*_s$ are assumed to be fixed regardless of the wave number k.

The wave number of the light is denoted by k. The positional coordinate z of the mirror is denoted by $z_0$. Further, r is the reflectivity of the mirror.

The phase (a fixed value) at z=0, which is determined according to the structure of the interferometer constituting the OCT apparatus, is denoted by $\phi$. The value of $\phi$ does not affect the following description, and therefore, it is assumed hereafter that $\phi=0$ for the sake of simplicity.

As is evident from Equation (6), the oscillation period ($=\pi/z_0$) of the optical intensity $I^*_c(k)$ of the interference light shortens as $z_0$ increases. Therefore, when $z_0$ increases, the vibration period of the interference light approaches the pixel width of the one-dimensional line sensor. In this case, the amplitude of the interference signal intensity $I^*_c(k)$ is averaged by the pixels. Hence, when $z_0$ is large, the amplitude of the signal outputted by the array scan camera decreases. Accordingly, the OCT signal obtained by subjecting Equation (6) to Fourier transform also decreases.

Meanwhile, the latter half part of the right side of Equation (1) is expressed by the following equation.

$$\exp\left[-\frac{w^2}{2\ln 2}\varsigma^2\right] \quad (7)$$

This equation expresses the effect of the reduction in the amplitude of the interference light $I^*_c(k)$ when the resolution of the spectroscopy unit approaches the wave number spacing of the pixels.

Similarly to Equation (6), Equation (7) is a function that decreases monochromatically as $z_0$ increases. Accordingly, this function also reaches a minimum at the maximum ranging depth ($z_0=z_{RD}$).

At the maximum ranging depth ($z_0=z_{RD}$), $\varsigma$ is fixed ($\pi/2$), and therefore the value of this function at the maximum ranging depth $z_{RD}$ is determined by w ($=\delta k/\Delta k$).

Incidentally, 0.104 nm (where $\lambda=1320$ nm) has been reported as the resolution $\delta\lambda$ of the spectroscopy unit employed in SD-OCT (S. H. Yun, G. J. Tearney, B. E. Bouma, B. H. Park, and J. F. de Boer, "High-speed spectral-domain optical coherence tomography at 1.3 μm wavelength", OPTICS EXPRESS, Vol. 11, p. 3598-3604, 2003.). On the other hand, 0.208 nm has been reported as the wavelength spacing $\Delta\lambda$ of the pixels. Hence, the resolution $\delta\lambda$ (0.104 nm) of the spectroscopy unit is smaller than the wavelength spacing $\Delta\lambda$ (0.208 nm) of the pixels. Meanwhile, the maximum ranging depth is 2.08 mm, as derived from Equation (3).

In this case, the value of Equation (7) in the maximum ranging depth (2.08 mm) is 0.64 (−1.9 dB).

Hence, the value of the relative peak intensity R ($z_0$) in the maximum ranging depth (2.08 mm) is 0.26 (=0.41×0.64; −5.9 dB). This decrease in the signal intensity is not sufficient to cause a dramatic decrease in the depth range.

However, when the wavelength spacing is narrowed to increase the maximum ranging depth, the conditions change drastically.

For example, when an attempt is made to increase the maximum ranging depth to 7.5 mm, the wavelength spacing of the pixels should be set at 0.058 nm (10 GHz following optical frequency conversion).

In this case, the wavelength spacing of the pixels becomes smaller than the resolution of the spectroscopy unit (0.104 nm). As a result, the relative peak intensity R($z_0$) in the maximum ranging depth becomes 0.0014 (−28.7 dB). In these conditions, the OCT signal is buried in noise and observation becomes impossible.

When an attempt is made to increase the depth range in this manner such that the wavelength spacing of the pixels narrows, the wavelength spacing of the pixels becomes smaller than the resolution of the spectroscopy unit. In this case, the oscillation period of the interference signal shortens when the mirror is in a deep position, and as a result, hence the oscillation period of the interference signal falls to or below there solution of the spectroscopy unit. Hence, the amplitude of the signal outputted from the array scan camera decreases, and as a result, the OCT signal also becomes smaller.

Accordingly, the OCT signal falls to or below the noise level, and the depth range becomes narrower than the maximum ranging depth.

(iii) Factors Limiting the Depth Range of OFDR-OCT (a) SS-OCT

First, the factors limiting the depth range of OFDR-OCT using a swept source (to be referred to hereafter as "SS-OCT") will be described. To simplify the description, it is assumed that the measurement object is constituted by a single mirror.

The optical intensity $I_c(k)$ of the interference light received by the photodetectors 60, 61 may be expressed as follows (S. H. Yun, G. J. Tearney, J. F. de Boer, N. Iftimia, and B. E. Bouma, "High-speed optical frequency-domian imaging", OPTICS EXPRESS, Vol. 11, p. 2953-2963, 2003.).

$$I_c(k)=I_r+I_s+2\sqrt{rI_rI_o}\Gamma(z_0)\cos(2kz_0+\phi) \quad (8)$$

Here, $\Gamma(z)$ is a coherent function of the light outputted by the tunable wavelength light generating apparatus 51. $I_r$ is the intensity of the reference light, $I_o$ is the intensity of the measurement light, and $I_s$ is the intensity of the signal light. The reflectivity of the mirror is denoted by r. The wave number of the light is denoted by k. The positional coordinate z of the mirror is denoted by $z_0$.

The phase (a fixed value) at z=0, which is determined according to the structure of the interferometer constituting the OCT apparatus, is denoted by $\phi$. The value of $\phi$ does not affect the following description, and therefore, it is assumed hereafter that $\phi=0$ for the sake of simplicity.

The coherent function $\Gamma(z)$ is an autocorrelation function of the photoelectric field. In other words, $\Gamma(z)$ denotes the intensity of interference light obtained by dividing light into two equal halves, causing one of the halves to travel 2z (an optical path length difference) from the other half, and then recombining the two halves. Note that $\Gamma(z)$ is normalized such that $\Gamma(0)=1$.

When the coherent function $\Gamma(z)$ is measured using an optical delay device (the optical delay device 11 in FIG. 14, for example) structured such that light goes and back along an optical path, z becomes half the distance (optical path length) by which the light goes and back.

The OCT signal of SS-OCT is obtained by subjecting Equation (8) to Fourier transform relative to the wave number k and calculating the squared absolute value thereof. Accordingly, the OCT signal of SS-OCT is proportional to $\Gamma^{-2}(z_0)$.

The coherent function $\Gamma(z)$ is often expressed by a function such as the following.

$$\Gamma(z) = \exp\left[-\frac{z^2}{l_c^2} \cdot \ln 2\right] \quad (9)$$

Here, $l_c$ is the value of z when the value of the function is ½, or in other words a coherence length.

The coherence length of a swept source used in SS-OCT is 3.2 mm (S. H. Yun, G. J. Tearney, J. F. deBoer, N. Iftimia, and B. E. Bouma, "High-speed optical frequency-domian imaging", *OPTICS EXPRESS*, Vol. 11, p. 2953-2963, 2003.). Note that value reported by S. H. Yun et al. is 6.4 mm which is obtained by doubling the coherence length.

When this type of light source is used, the value of the coherent function in a maximum ranging depth of 7.5 mm is 0.022 (−16.5 db).

Meanwhile, the wave number of the light outputted from the swept source changes continuously. Hence, similarly to SD-OCT, a reduction in the OCT signal caused by averaging of the amplitude of the interference light intensity should be taken into account.

The effect on the OCT signal caused by this reduction is expressed by Equation (5), as is the case with SD-OCT. The value of this equation in the maximum ranging depth is 0.41 (−3.9 db).

Hence, the OCT signal in the maximum ranging depth (7.5 mm) is 0.009 times (−16.5 db−3.9 db=−20.5 db) the OCT signal in a position of z=0.

This large decrease in the OCT signal causes the OCT signal to become buried in noise such that observation is impossible. Accordingly, the depth range becomes narrower than the maximum ranging depth.

(b) OFDR-OCT Using SSG-DBR Laser

The coherence length of laser light outputted by an SSG-DBR laser is 10 m or more. Hence, the coherence length is considerably greater than the maximum ranging depth. Therefore, the OCT signal in the maximum ranging depth does not fall to or below noise level.

However, the coherence length is too long, and therefore reflection light generated in various locations within the OCT apparatus interferes with the reference light, so that noise is generated. This noise (to be referred to as interference noise hereafter) raises the noise level of the OCT signal, i.e. the reflectivity profile.

Hence, even though the OCT signal does not decrease in the maximum ranging depth, the depth range of OFDR-OCT using an SSG-DBR laser as a light source is narrow.

(First Invention)

To achieve the objects described above, a first aspect of the present invention is an optical coherence tomography apparatus having: a broadband light generating device for outputting light simultaneously in all wave numbers within a predetermined range; an optical divider for dividing output light of the broadband light generating device into measurement light and reference light; a light-irradiating and light-trapping unit for irradiating a measurement object with the measurement light and trapping signal light composed of the measurement light reflected or backscattered by the measurement object; an optical coupler for combining the signal light and the reference light; an optical demultiplexer for dividing output light of the coupler into a plurality of predetermined wave number sections and outputting divided output light simultaneously; a group of photo-detecting devices provided in each of the predetermined wave number sections, for measuring an intensity of output light of the optical demultiplexer; and a computing and control apparatus for specifying, on the basis of output of the group of photo-detecting devices, a reflection position or backscattering position and a reflection intensity or backscattering intensity of the measurement light relative to an irradiation direction of the measurement light on the measurement object.

(Second Invention)

To achieve the objects described above, a second aspect of the present invention pertaining to the first aspect, an optical-divider and optical-coupler serves as the optical divider and the optical coupler.

(Third Invention)

To achieve the objects described above, a third aspect of the present invention has another optical demultiplexer having a substantially identical structure to the optical demultiplexer, for dividing another output light of the coupler into the plurality of predetermined wave number sections and outputting divided output light simultaneously, and has a group of photo-detecting devices provided in each of said predetermined wave number sections in place of said photo-detecting devices, for measuring a difference between a first optical intensity of output light of said optical demultiplexer and a second optical intensity of output light of said another optical demultiplexer.

(Fourth Invention)

To achieve the objects described above, in a fourth aspect of the present invention pertaining to the first aspect, the computing and control apparatus subjects a function expressing a relationship between an intensity of light outputted by the optical coupler and the wave number, which is obtained on the basis of the output of the group of photo-detecting devices, to Fourier transform relative to the wave number, and squares an absolute value thereof.

(Fifth Invention)

To achieve the objects described above, in a fifth aspect of the present invention pertaining to the first aspect, the plurality of predetermined wave number sections are a plurality of wave number sections having an identical wave number width and separated into equal intervals.

(Sixth Invention)

To achieve the objects described above, a sixth aspect of the present invention pertaining to the first aspect has a multichannel analog to digital converter for receiving a plurality of analog electric signals outputted by the group of photo-detecting devices simultaneously, and converting the analog signals into digital signals simultaneously; and a computing and control apparatus for specifying, on the basis of an output signal of the multichannel analog to digital converter, a reflection position or backscattering position and a reflection intensity or backscattering intensity of the measurement light relative to an irradiation direction of the measurement light on the measurement object.

(Seventh Invention)

To achieve the objects described above, a seventh aspect of the present invention pertaining to the first through sixth aspects has an optical amplifier for amplifying the signal light.

(Eighth Invention)

To achieve the objects described above, in an eighth aspect of the present invention pertaining to the first through sixth aspects, a full width at half maximum of a transmission characteristic spectrum of the demultiplexer relative to a wave number in each of the predetermined wave number sections is narrower than a width of each wave number section and greater than 0.2 times the width of each wave number section.

(Ninth Invention)

To achieve the objects described above, a ninth aspect of the present invention pertaining to the first through sixth aspects has an optical filter for shaping the output light of the broadband light generating device such that an optical intensity at each end of each of the predetermined wave number sections is smaller than an optical intensity in the center of each of the predetermined wave number sections, and outputting the shaped output light to the optical divider.

(Tenth Invention)

To achieve the objects described above, a tenth aspect of the present invention pertaining to the first through sixth aspects has, in place of the broadband light generating device, a comb optical generator for outputting light steadily and simultaneously in each of the predetermined wave number sections such that an optical intensity at each end of each of the predetermined wave number sections is smaller than an optical intensity in the center of each of the predetermined wave number sections.

(Eleventh Invention)

To achieve the objects described above, an eleventh aspect of the present invention is an optical coherence tomography apparatus having a broadband light generating device for outputting light steadily and simultaneously in all wave numbers within a predetermined range from a first output port; an optical divider, a first input port of which is optically connected to the first output port of the broadband light generating device, for dividing output light of the broadband light generating device into measurement light and reference light, outputting the measurement light from a second output port, and outputting the reference light from a third output port; a light-irradiating and light-trapping unit, a second input port of which is optically connected to the second output port of the optical divider, for irradiating a measurement object with the measurement light and trapping signal light composed of the measurement light reflected or backscattered by the measurement object, and outputting the signal light from a fourth output port; an optical delay device, a third input port of which is optically connected to the third output port of the optical divider, for delaying the reference light and outputting delayed output light from a fifth output port; an optical coupler, a fourth input port of which is optically connected to the fourth output port of the light-irradiating and light-trapping unit, and a fifth input port of which is optically connected to the fifth output port of the optical delay device, for combining the signal light and the reference light and outputting combined output light from a sixth output port; an optical demultiplexer, a sixth input port of which is optically connected to the sixth output port of the coupler, for dividing output light of the optical coupler into a plurality of predetermined wave number sections and outputting divided output light simultaneously from a plurality of seventh output ports; a plurality of photo-detecting devices, seventh input ports of which are optically connected individually to the plurality of seventh output ports of the optical demultiplexer, for photoelectrically converting and outputting output signal outputted from each of the seventh output ports; and a computing and control apparatus for specifying, on the basis of output of the plurality of photo-detecting devices, a reflection position or backscattering position and a reflection intensity or backscattering intensity of the measurement light relative to an irradiation direction of the measurement light on the measurement object.

(Twelfth Invention)

To achieve the objects described above, in a twelfth aspect of the present invention pertaining to the eleventh aspect, the computing and control apparatus subjects a function expressing a relationship between an intensity of light outputted by the optical coupler and the wave number, which is obtained on the basis of the output of the group of photo-detecting devices, to Fourier transform relative to the wave number, and squares an absolute value thereof.

(Thirteenth Invention)

To achieve the objects described above, in a thirteenth aspect of the present invention pertaining to the eleventh aspect, the plurality of predetermined wave number sections are a plurality of wave number sections having an identical wave number width and separated into equal intervals.

(Fourteenth Invention)

To achieve the objects described above, a fourteenth aspect of the present invention pertaining to the eleventh aspect has a multichannel analog to digital converter, a plurality of input terminals of which are connected individually to respective first output terminals of the plurality of photo-detecting devices, for receiving analog electric signals outputted by each of the plurality of photo-detecting devices simultaneously, converting the analog signals into digital signals simultaneously, and outputting the digital signals to a second output terminal; and a computing and control apparatus, a second input terminal of which is connected to the second output terminal of the multichannel analog to digital converter, for specifying, on the basis of the digital signals outputted by the multichannel analog to digital converter, a reflection position or backscattering position and a reflection intensity or backscattering intensity of the measurement light relative to an irradiation direction of the measurement light on the measurement object.

(Fifteenth Invention)

To achieve the objects described above, a fifteenth aspect of the present invention pertaining to the eleventh through fourteenth aspects of the present invention has an optical amplifier, wherein an eighth input port of the optical amplifier is optically connected to the fourth output port of the light-irradiating and light-trapping unit instead of the fourth input port of the optical coupler, an eighth output port of the optical amplifier is optically connected to the fourth input port of the optical coupler instead of the fourth output port of the optical unit, and the optical amplifier amplifies the signal light inputted from the eighth input port, and outputs the amplified signal light to the eighth output port.

(Sixteenth Invention)

To achieve the objects described above, in a sixteenth aspect of the present invention pertaining to the eleventh through fourteenth aspects of the present invention, a full width at half maximum of a transmission characteristic spectrum of the demultiplexer relative to a wave number in each of the predetermined wave number sections is narrower than a width of each wave number section and greater than 0.2 times the width of each wave number section.

(Seventeenth Invention)

To achieve the objects described above, a seventeenth aspect of the present invention pertaining to the eleventh through fourteenth aspects of the present invention has an optical filter, wherein a ninth input port of the optical filter is optically connected to the first output port of the broadband light generating device instead of the first input port of the optical divider, a ninth output port of the optical filter is optically connected to the first input port of the optical divider instead of the first output port of the broadband light generating device, and the optical filter shapes, in each of the predetermined wave number sections, the output light of the broadband light generating device, which is inputted from the ninth input port, into light having a full width at half maximum that is narrower than a width of each of the predetermined wave number sections, and then outputs the light to the ninth output port.

(Eighteenth Invention)

To achieve the objects described above, an eighteenth aspect of the present invention pertaining to the eleventh through fourteenth aspects of the present invention has, in place of the broadband light generating device, a comb optical generator for outputting light steadily and simultaneously in each of the predetermined wave number sections such that an optical intensity at each end of each of the predetermined wave number sections is smaller than an optical intensity in the center of each of the predetermined wave number sections.

According to the present invention, interference light is spectrally divided by an optical demultiplexer, and a spectrum of the interference light is measured at high speed by a photodetector connected to each channel of the optical demultiplexer. Thus, the OCT measurement speed is increased beyond that of conventional FD-OCT by at least two digits. Moreover, the effective coherence length of the interference light can be lengthened by the optical demultiplexer, and therefore, the depth range may be enlarged beyond that of conventional FD-OCT.

DESCRIPTION OF EMBODIMENTS

Embodiments of the present invention will be described below in accordance with the drawings. Note, however, that the technical scope of the present invention is not limited to these embodiments, and extends to the matter described in the claims and equivalents thereof. Note that identical parts have been allocated identical reference symbols, and duplicate description thereof has been omitted.

Figure 1:
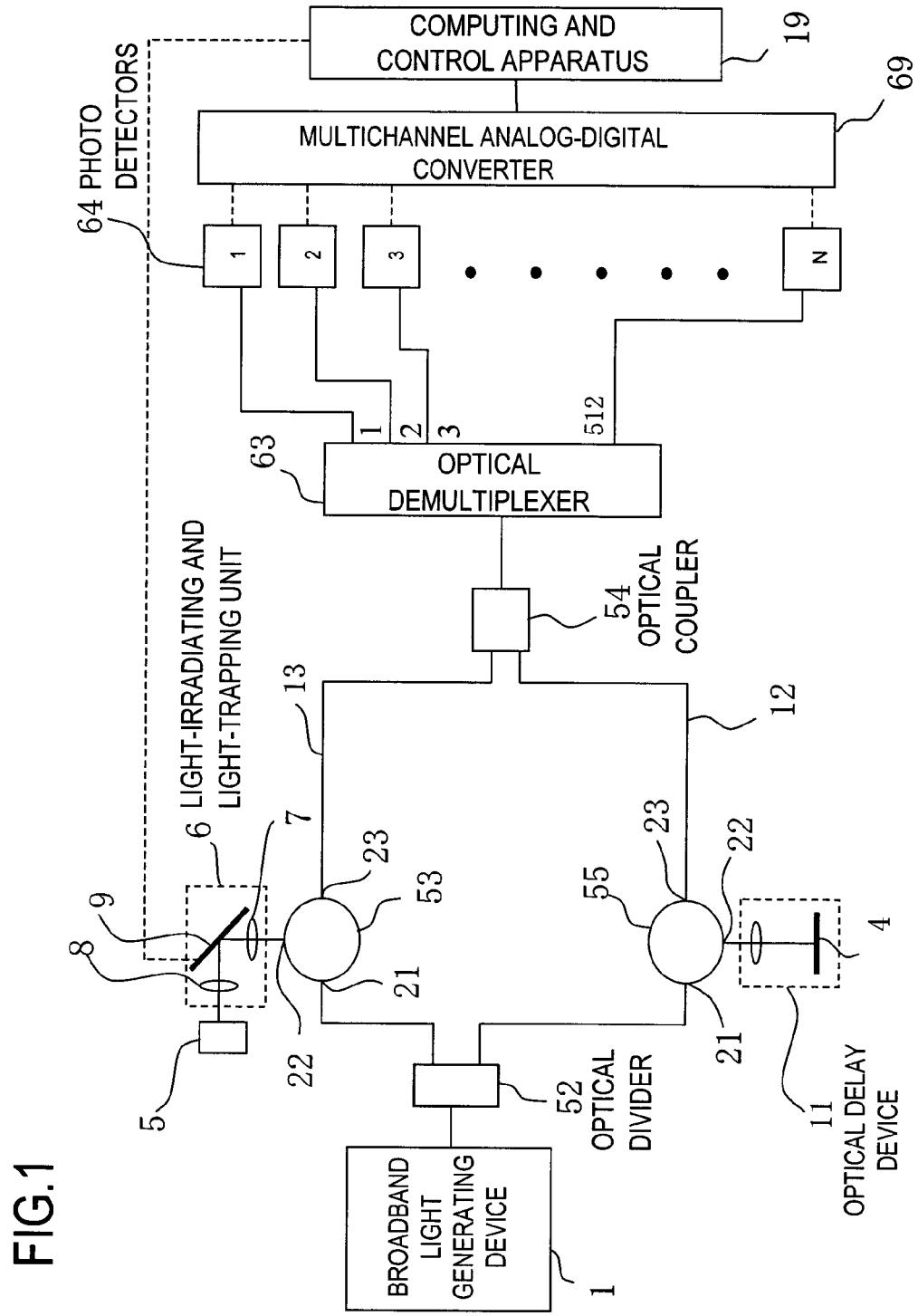
FIG. 1 is a block diagram showing the main parts of an optical coherence tomography apparatus according to a first embodiment.

As shown in FIG. 1, an optical coherence tomography apparatus according to this embodiment uses a broadband light generating device 1 such as a super luminescent diode (SLD) as a light source.

The broadband light outputted by the broadband light generating device 1 is divided into reference light and measurement light by an optical divider 52. Next, signal light generated when the measurement light is backscattered by a measurement object 5 and the reference light are combined in an optical coupler 54 to form interference light. This interference light is spectrally divided by an optical demultiplexer 63 such as an AWG (Arrayed-Waveguide Grating).

A plurality of photo-detecting devices 64 are optically connected individually to a plurality of light output ports of the optical demultiplexer 63. The respective photo-detecting devices 64 subject the output light of the optical demultiplexer 63 to photoelectric conversion. Electric signals generated by this photoelectric conversion are inputted into a multichannel analog to digital converter 69. The multichannel analog to digital converter 69 converts the plurality of input analog electric signals into digital signals simultaneously.

Incidentally, in conventional FD-OCT, the measurement time is limited by the time required to measure the spectral characteristic of the interference light.

More specifically, in SD-OCT, the measurement time is limited by the time required for the CCD array scan camera 17 to subject the interference light that is spectrally divided by the diffraction grating 15 to photoelectric conversion and output the electric signal generated by the photoelectric conversion to the data acquisition board 18. Meanwhile, in OFDR-OCT, the measurement time is limited by the time required for the tunable wavelength light generating apparatus 51 to change the wave number of the output light in order to measure the spectral characteristic of the interference light.

In this embodiment, on the other hand, the time required to measure the spectral characteristic of the interference light corresponds to the time required for the photo-detecting devices 64 to subject the interference light to photoelectric conversion, and for the multichannel analog to digital converter 69 to convert the analog electric signals generated by the photoelectric conversion into digital signals.

In this embodiment, the plurality of photo-detecting devices 64 subject the interference light to photoelectric conversion simultaneously, and therefore the time required to subject the interference light to photoelectric conversion is negligible.

Hence, the majority of the time required to measure the spectral characteristic of the interference light is the time required for the multichannel analog to digital converter 69 to convert the analog electric signals generated by the photoelectric conversion into digital signals.

However, the time required for the latest multichannel analog to digital converter 69 to convert an analog electric signal into a digital signal is extremely short. Moreover, a multichannel analog to digital converter is capable of converting several hundred analog electric signals into digital signals simultaneously.

Hence, according to this embodiment, the spectral characteristic of the interference light can be measured in an extremely short amount of time. As a result, the OCT measurement time can be made extremely short.

In this embodiment, the optical coherence tomography apparatus includes the optical demultiplexer 63, which divides the output light of the optical coupler 54, or in other words input light, into each of a plurality of predetermined wave number sections (channels) and outputs the divided light simultaneously, the group of photo-detecting devices 64 provided for each channel of the optical demultiplexer 63, which measure the intensity of the light outputted from the optical demultiplexer 63, and the multichannel analog to digital converter 69, which receives the analog electric signals outputted by the respective photo-detecting devices 64 simultaneously and converts these analog signals into digital signals simultaneously. Therefore, the spectral characteristic of the interference light can be measured in an extremely short amount of time.

Hence, according to this embodiment, the FD-OCT measurement time can be reduced greatly. As a result, a three-dimensional moving tomographic image can be observed.

Meanwhile, the wave number dependence (spectrum) of the intensity of the output light outputted from the respective output ports of the optical demultiplexer 63 may be adjusted by altering the structure of the optical demultiplexer 63. Accordingly, the full width at half maximum of the spectrum of the light that is outputted from the respective output ports of the optical demultiplexer 63 can be made narrower than the width of the wave number section (channel) of the light outputted from each output port.

In this embodiment, it is also possible to make the full width at half maximum of the transmittance spectrum relative to the wave number narrower than the channel width in each channel of the optical demultiplexer, or in other words to make the full width at half maximum of the transmittance spectrum relative to the wave number narrower than the width of each wave number section, in each wave number section (channel) of the optical demultiplexer.

Hence, according to this embodiment, the effective coherence length of the interference signal can be lengthened, so that even in the maximum ranging depth, the interference signal intensity exhibits substantially no decrease. Therefore, according to this embodiment, the depth range can be made deeper than that of conventional FD-OCT, and deep living tissue can be observed.

Furthermore, by providing an optical filter 78 for outputting the output light to the optical divider, which shapes the output light of the broadband light generating device such that the optical intensity at the two ends of each of the predetermined wave number sections is smaller than the optical intensity in the center of each of the predetermined wave number sections, loss in the signal light produced by the optical demultiplexer can be reduced, and as a result, the measurement sensitivity can be improved.

The sensitivity can also be improved by amplifying the signal light using an optical amplifier 82. Note that the OCT according the present invention will be referred to as OD-OCT (Optical Demultiplexer OCT).

First Embodiment

This embodiment relates to an optical coherence tomography apparatus in which the A-line scan rate is at least one hundred times greater than that of conventional FD-OCT.

(1) Apparatus Constitution

First, the constitution of the optical coherence tomography apparatus according to this embodiment will be described.

As shown in FIG. 1, an OCT apparatus according to this embodiment has a broadband light generating device 1 composed of a super luminescent diode (SLD). A light output port of the broadband light generating device 1 is optically connected to a light input port of a first coupler 52 (optical divider) composed of a directional coupler for dividing light into two (at 10:90, for example).

A first light output port (on the 90% divided proportion side) of the first coupler 52 is optically connected to a light input port 21 of a first optical circulator 53. A light-output and light-input port 22 of the optical circulator 53 is connected to a light-irradiating and light-trapping unit 6 for irradiating a measurement object 5 with measurement light and trapping signal light reflected by the measurement object 5. A light output port 23 of the optical circulator 53 is connected to a first light input port of a second coupler 54 (optical coupler) composed of a directional coupler (with a division ratio of 50:50).

The light-irradiating and light-trapping unit 6 includes a collimator lens 7 for shaping the measurement light outputted from the light-output and light-input port 22 of the optical circulator 53 into parallel beams, a focusing lens 8 for converging the parallel beams into the measurement object 5, and a galvanometer mirror 9 for scanning the surface of the measurement object 5 with the measurement light along a straight line by deflecting the measurement light.

A second light output port (on the 10% divided proportion side) of the first coupler 52 is optically connected to the light input port 21 of an optical circulator 55. The light-output and light-input port 22 of the optical circulator 55 is optically connected to an optical delay device 11 for delaying the reference light outputted from an optical fiber end portion by causing the reference light to go from the optical fiber end portion to a reference mirror 4 and back. The reference mirror 4 is supported by a support so as to be capable of moving forward and backward, and the position thereof is adjusted such that the optical path lengths of a reference arm 12 and a sample arm 13 are substantially equal.

The light output port 23 of the optical circulator 55 is optically connected to a second light input port of the second coupler 54 composed of a directional coupler (with a division ratio of 50:50). A light output port of the second coupler 54 is optically connected to a light input port of the optical demultiplexer 63, which is composed of an AWG (arrayed-waveguide grating).

The plurality of light output ports of the optical demultiplexer 63 are optically connected individually to the light input ports of the plurality of photo-detecting devices 64, namely photodetectors, for subjecting received optical signals to photoelectric conversion and outputting the resulting electric signals.

Output terminals of the photo-detecting devices 64 are connected individually to input terminals (channels) of the multichannel analog to digital converter 69.

An output terminal of the multichannel analog to digital converter is electrically connected to an input terminal of a computing and control apparatus 19, namely a computer, for calculating the reflectivity profile, or in other words the distribution of the reflection light intensity or backscattered light intensity. An output portion of the computing and control apparatus 19 is electrically connected to an input portion of a display apparatus (not shown) such as a monitor or a printer for displaying calculation results. The computing and control apparatus 19 controls the galvanometer mirror 9 of the light-irradiating and light-trapping unit 6 on the basis of input information.

Here, the center wavelength of the SLD is 1550 nm, and the full width at half maximum thereof is 50 nm. Further, the number of channels in the AWG, i.e. the number of light output ports, is 512.

Figure 2:
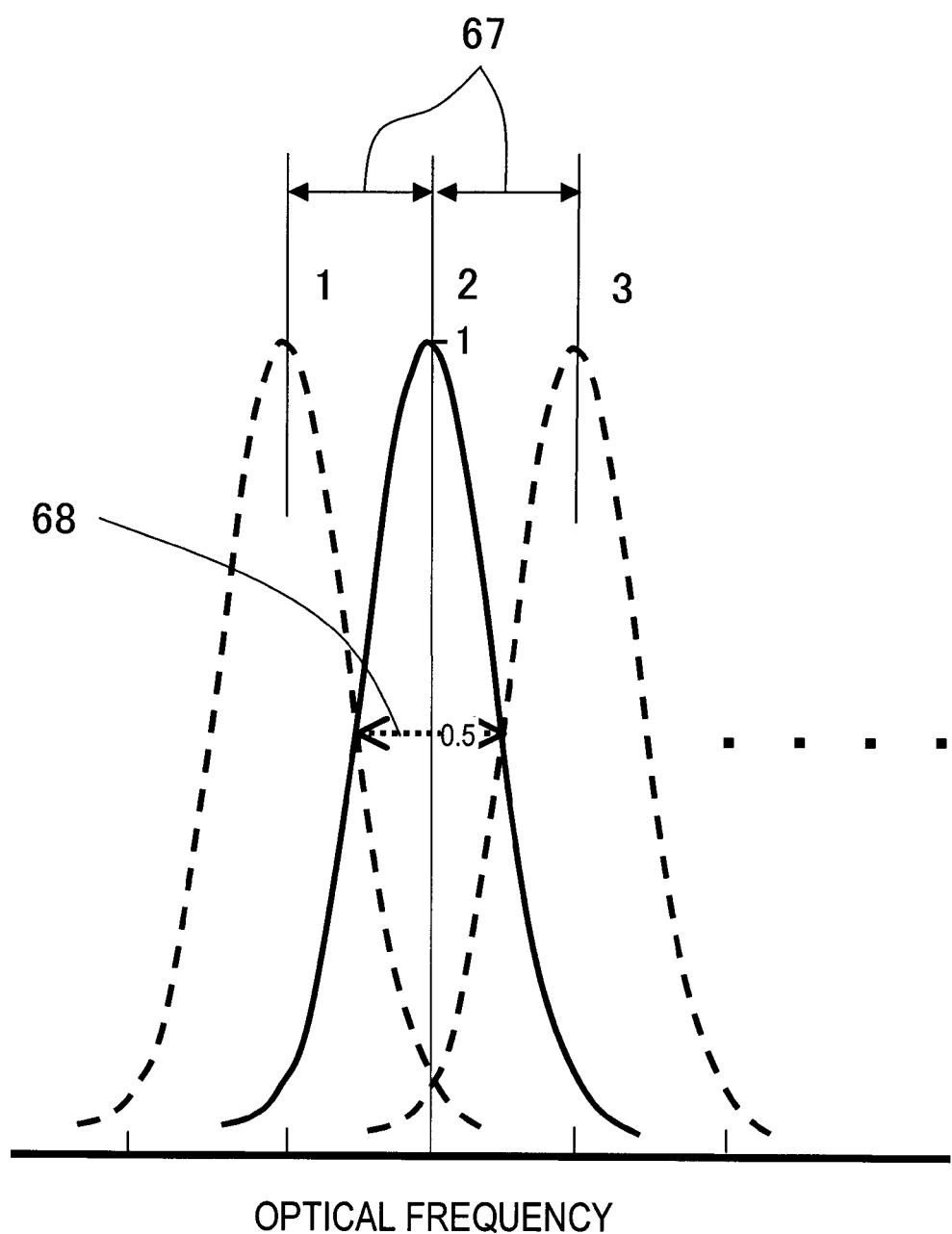
FIG. 2 is a spectrum of output light from an optical demultiplexer according to the first embodiment.

As shown in FIG. 2, a channel spacing 67 of each channel in the optical demultiplexer 63 is 10 GHz. A full width at half maximum 68 of the transmittance spectrum of each channel is also 10 GHz. Hence, each channel (wave number section) has an identical frequency width (in other words, an identical wave number width), and the channels are separated by equal intervals.

Further, the response speed of the photo-detecting devices 64 is 0.1 ns. The photo-detecting devices 64 are individually connected to one of the output ports of the AWG. Accordingly, the number of the photo-detecting devices 64 is 512. The number of input terminals of the multichannel analog to digital converter 69, to which the output terminals of the photo-detecting devices 64 are connected individually, is also 512.

The analog-digital conversion rate of the multichannel analog to digital converter 69, or in other words the sampling frequency, is 60 MHz. In other words, the sampling time is 16.7 ns. The multichannel analog to digital converter 69 subjects an electric signal inputted from each input terminal to analog-digital conversion (i.e. digitization) within the sampling time, and records the resulting digital signals in a built-in recording apparatus. The digital signals recorded in the recording apparatus are output to the computing and control apparatus 19 in sequence.

(2) Operation

Next, an operation of the optical coherence tomography apparatus according to this embodiment will be described.

Light outputted from the broadband light generating device 1 is divided into two in a ratio of 10:90 by the first coupler 52 (optical divider). One part of the divided light (measurement light) is led to the light-irradiating and light-trapping unit 6 by the first optical circulator 53.

The measurement light incident on the light-irradiating and light-trapping unit 6 is emitted onto the measurement object 5 by the light-irradiating and light-trapping unit 6. The measurement light emitted onto the measurement object 5 is reflected by the surface and the interior of the measurement object 5. A part of the reflected light is trapped in the light-irradiating and light-trapping unit 6 to form signal light.

The signal light is led to the first light input port of the second coupler 54 (optical coupler) by the first optical circulator 53.

The other part of the light divided by the optical divider 52 (reference light) is led to the optical delay device 11 by the optical circulator 55. The reference light is caused to travel a predetermined optical path length in the optical delay device 11, and is then led to the second light input port of the second coupler 54 (optical coupler) by the second optical circulator 55.

The signal light and reference light are combined by the second coupler 54 (optical coupler) to form interference light. The interference light is led to the optical demultiplexer 63.

The interference light incident on the optical demultiplexer 63 is separated into light beams having a frequency width of 10 GHz, as shown in FIG. 2, by the optical demultiplexer 63.

In other words, the interference light is spectrally divided by the optical demultiplexer 63. The spectrally divided interference light is outputted from the individual light output ports of the optical demultiplexer 63.

The abscissa of FIG. 2 shows the frequency of the light, and the ordinate shows the transmittance of the light. The peaks shown in the drawing are the transmittance spectra of the output light from each light output port of the optical demultiplexer 63. The numeral allocated to each peak is the light output port number, and numerals are allocated in order from the output light with the lowest frequency.

The interference light outputted from the output ports of the optical demultiplexer 63 is led to the photo-detecting devices 64 that are optically connected to each of the output port. The interference light led to each photo-detecting device 64 is subjected to photoelectric conversion to form an electric signal. The electric signals outputted individually from the photo-detecting devices 64 are inputted individually into the input terminals of the multichannel analog to digital converter 69.

The electric signals inputted into the input terminals of the multichannel analog to digital converter 69 are converted into digital signals. The digital signals are recorded in the built-in recording apparatus of the multichannel analog to digital converter 69. The digital signals recorded in the recording apparatus are outputted from the multichannel analog to digital converter 69 in sequence. The digital signals outputted from the multichannel analog to digital converter 69 are inputted into the computing and control apparatus 19. The computing and control apparatus 19 calculates a reflectivity profile on the basis of the input digital signals.

Every time a sequence (in which the interference light is subjected to photoelectric conversion by the photo-detecting devices 64, the photoelectric-converted signals are digitized by the multichannel analog to digital converter 69, the digitized signals are transferred to the computing and control apparatus 19, and the transferred signals are recorded) is finished, the computing and control apparatus 19 transmits a command to the galvanometer mirror 9 so as to move the measurement light irradiation position slightly (by 25 μm, for example) along a straight line on the measurement object 5.

On the basis of the data recorded in this manner, the computing and control apparatus 19 calculates a reflectivity profile and constructs a tomographic image by amalgamating the reflectivity profiles obtained along the straight line on the measurement object 5.

At this time, the computing and control apparatus 19 calculates the reflectivity profile in the following manner.

The optical demultiplexer 63 spectrally divides the incident light and outputs light having different optical frequencies (wave numbers) individually from the plurality of output ports. Here, the center wave number (a central value of the wave numbers of the light outputted from each channel) of the interference light outputted from an $i^{th}$ output port is assumed to be $k_i$. Further, the intensity (integrated intensity) of the light outputted from the $i^{th}$ output port is assumed to be $I_i$. More precisely, the intensity $I_i$ of the light is a value obtained when an electric signal obtained by subjecting the interference light outputted from the $i^{th}$ output port to photoelectric conversion using the detector 64 is digitized by the digital converter 69.

The computing and control apparatus 19 subjects $I_i$ to Fourier transform relative to $k_i$, and the squared absolute values thereof is calculated. The result of the squared absolute values calculated in this manner corresponds to the reflectivity profile of the measurement light.

More specifically, $I_i$ is subjected to discrete Fourier transform according to the following Equations (10) and (11), and $F_r^2(z)$, which is the squared absolute value thereof, is determined by Equation (12).

$$F_c(z) = \sum_{i=1}^{N} I_i \cdot \cos(2k_i z) \qquad (10)$$

$$F_s(z) = \sum_{i=1}^{N} I_i \cdot \sin(2k_i z) \qquad (11)$$

$$F_r^2(z) = F_c(z)^2 + F_s(z)^2 \qquad (12)$$

The above equations are identical to the equations for calculating the reflectivity profile that are used in OFDR-OCT (T. Amano, H. Hiro-oka, D. Choi, H. Furukawa, F. Kano, M. Takeda, M. Nakanishi, K. Shimizu, and K. Ohbayashi, "Optical frequency-domain reflectormetry with a rapid wavelength-scanning superstructure-grating distributed Bragg reflector laser", *APPLIED OPTICS*, Vol. 44, p. 808-816, 2004.). Note that N is the total number of wave number sections into which the optical demultiplexer 63 divides the interference light.

The response speed of the photo-detecting devices 64 is 0.1 ns, and the sampling time of the multichannel analog to digital converter 69 (in other words, the time required for analog-digital conversion) is 16.7 ns. Hence, the A-line scan period in this embodiment is 16.8 ns. In other words, the A-line scan rate is 60 MHz (=1/16.8 ns). This value is greater than the maximum A-line scan rate (58 kHz) of conventional FD-OCT by two digits.

Hence, according to the optical coherence tomography apparatus of this embodiment, the A-line scan rate is at least one hundred times greater than that of conventional FD-OCT.

Note that the maximum ranging depth of this embodiment is 7.5 mm. This value is obtained by converting the channel spacing of 10 GHz into the wave number spacing $\Delta k$ and inserting the result into Equation (3).

Second Embodiment

This embodiment relates to an optical coherence tomography apparatus that is capable of capturing a three-dimensional moving tomographic image.

The apparatus constitution is basically identical to that of the optical coherence tomography apparatus of the first embodiment, shown in FIG. 1. Note, however, that the light-irradiating and light-trapping unit 6 is constituted differently, as shown in FIG. 3.

Figure 3:
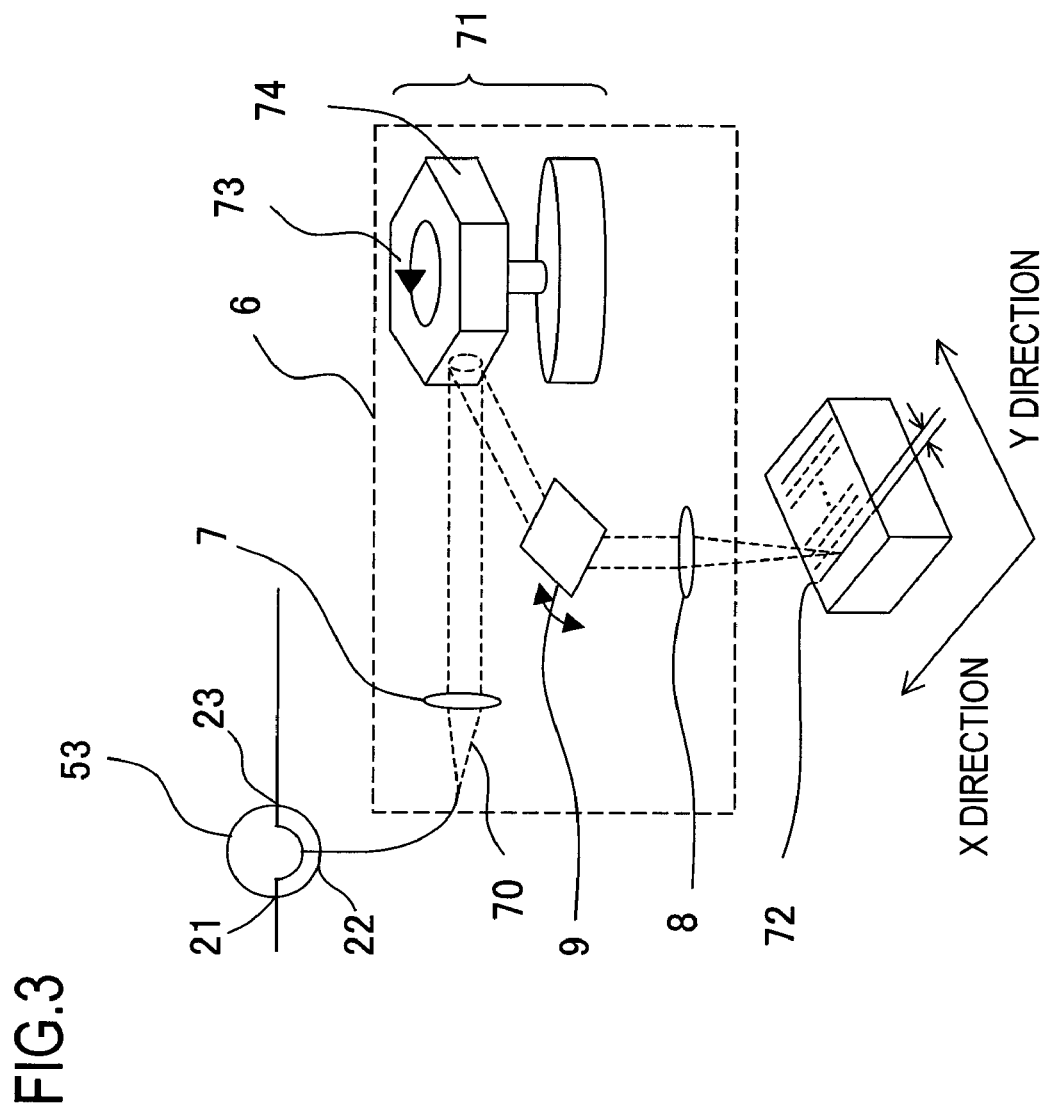
FIG. 3 is a block diagram of a light-irradiating and light-trapping unit of an optical coherence tomography apparatus according to a second embodiment.

As shown in FIG. 3, the light-irradiating and light-trapping unit 6 of this embodiment includes the collimator lens 7 for shaping measurement light 70 outputted from the light-output and light-input port of the optical circulator 53 into parallel beams, the focusing lens 8 for converging the parallel beams on a measurement object 5, a polygon scanner 71 for scanning the surface of the measurement object 5 with the measurement light along a scanning line 72 by deflecting the measurement light in a single direction (for example, an X direction in FIG. 3), and the galvanometer mirror 9 for moving the scanning line 72 slightly (by 10 μm, for example) in a perpendicular direction (a Y direction in FIG. 3) every time a single scan by the polygon scanner 71 ends.

The operation of the optical coherence tomography apparatus according to this embodiment differs from the operation of the optical coherence tomography apparatus according to the first embodiment in that the polygon scanner 71 performs a scan along the scanning line 72 in a lateral direction (X direction) with the measurement light, the scanning line 72 is scanned gradually in a perpendicular direction (Y direction) by the galvanometer mirror 9 in order to capture a three-dimensional tomographic image, and the computing and control apparatus 19 constructs a three-dimensional tomographic image on the basis of data obtained from the measurement light lateral scan and the perpendicular direction scan.

The perpendicular direction scan of the scanning line 72 is performed when a single scan along the scanning line 72 in the lateral direction of the measurement light is complete and the measurement data required to construct a two-dimensional tomographic image is obtained. The computing and control apparatus 19 constructs a three-dimensional tomographic image by arranging the two-dimensional tomographic images obtained in lateral direction scanning of the measurement light in order in the perpendicular direction.

As will be described below, when this apparatus is used, a single three-dimensional tomographic image can be captured in a short amount of time, namely 4.0 ms. Accordingly, a three-dimensional moving tomographic image can be captured.

The A-line scan rate of the optical coherence tomography apparatus according to this embodiment is the same as that of the first embodiment, i.e. 60 MHz. In other words, the time required for a single A-line scan is 16.8 ns.

As noted above, the lateral direction scanning of the measurement light required to capture a two-dimensional tomographic image is performed by the polygon scanner 71.

The rotation speed of the polygon scanner 71 is 40,000 revolutions per minute. Further, ninety-six polygon mirrors 74 are adhered to a rotary body 73 of the polygon scanner 71. Hence, the lateral direction scan is performed 64,000 times per second (40,000 revolutions÷60 seconds×96 surfaces= 64,000 times). In other words, 64,000 tomographic images are captured every second.

To construct a three-dimensional tomographic image, 256 tomographic images are captured while moving the scanning line 72 gradually in the perpendicular direction. Hence, the time required to construct a three-dimensional tomographic image is 4.0 ms (=15.625 μs×256).

In such a short time period, living tissue movement can be ignored. Hence, according to this embodiment, a moving image of living tissue can be captured.

Incidentally, in the example described above, the time required for a single lateral direction scan is 15.625 μs (=1 second÷64,000 times). Therefore, the number of A-line scans repeated on a single scanning line 72 is 930 (=15.625 μs÷16.8 ns).

Hence, the pixel count in the lateral direction of the three-dimensional image is 930. Meanwhile, the pixel count in the depth direction is half the number of sampled wave numbers, or in other words half the number of channels (light output ports) in the optical demultiplexer, according to Nyquists's theorem. Accordingly, the depth direction pixel count is 256 (=512/2).

Third Embodiment

This embodiment relates to an optical coherence tomography apparatus having a deeper depth range than that of conventional FD-OCT.

The optical coherence tomography apparatus of this embodiment differs from that of the first embodiment in that the full width at half maximum of the transmittance of each channel in the optical demultiplexer 63 is ⅔ of the channel spacing (10 GHz) between the channels (in the first embodiment, the full width at half maximum of the transmittance of each channel in the optical demultiplexer 63 is equal to the channel spacing between the channels).

As a result, the amplitude of the signal detected by the photo-detecting device 64 does not decrease even in the maximum ranging depth. Therefore, in this embodiment, the depth range is greater than the depth range of conventional FD-OCT. The reason for this is as follows.

The reference light and signal light combined by the second coupler (optical coupler) interfere only between spectral components having equal wave numbers k. Hence, the optical intensity density $I^*_c(k)$ of the interference light generated by the second coupler (optical coupler) is provided by the following equation. Note that in order to simplify the description, the wave number will be used hereafter as a variable instead of the optical frequency.

$$I^*_c(k) = I^*_r + I^*_s + 2\int \sqrt{I^*_r \cdot I^*_s(z)} \cos(2kz + \phi) dz \qquad (13)$$

Here, z is a depth direction coordinate of which a starting point is equal to the point at which the optical path lengths of the sample arm becomes equal to that of the reference arm. $I^*_r$ is the optical intensity density of the reference light. $I^*_s(z)$ is the optical intensity density of the signal light, and serves as a function of the position z in which the reflective surface exists.

$I^*_r$ and $I^*_s(z)$ are assumed to be fixed regardless of the wave number. The reason for this assumption is that when an SLD is used as the broadband light source 1, the optical intensity density of the light source varies slowly in accordance with the wave number, and therefore, by assuming that $I^*_r$ and $I^*_s(z)$ are fixed relative to the wave number, they have no effect on the following description.

The phase at z=0, which is determined according to the structure of the interferometer constituting the OCT apparatus, is denoted by $\phi$. The value of $\phi$ does not affect the following description, and is therefore assumed to be zero.

When the measurement object is a single mirror having a reflectivity r and positioned at a depth of $z=z_0$, the intensity of the signal light becomes $I^*_s(z) = r \times I^*_o \delta(z-z_0)$ where $I^*_o$ is the optical intensity density of the measurement light.

By inserting this expression into Equation (13) the following equation is obtained.

$$I^*_c(k) = I^*_r + I^*_s + 2\sqrt{rI^*_r I^*_o} \cos(2kz_0) \qquad (14)$$

The reflective surface of actual living tissue may be considered continuously distributed. Therefore, an interference signal from the living tissue is obtained by superposing signals according to Equation (14). Hence, by investigating the behavior of an OCT signal generated by a single mirror, the behavior of an OCT signal from living tissue can be learned.

The transmittance of the $i^{th}$ channel of the optical demultiplexer 63 is provided by the following equation (K. Okamoto "Fundamentals of Optical Waveguides", Academic Press, Amsterdam (2006), pp. 417-534.).

$$w_i(k) = \exp\left[-\frac{(k-k_i)^2}{2\sigma_w^2}\right] \qquad (15)$$

Here, $k_i$ is the center wave number of the $i^{th}$ channel.

The half width at half maximum of this transmittance function is $(2 \ln 2)^{1/2} \times \sigma_w$.

Hence, the intensity $I_i$ (integrated intensity) of the interference light outputted from the $i^{th}$ channel of the optical demultiplexer 63 is obtained by multiplying the optical intensity density of the interference light, expressed by Equation (14), by Equation (15), and integrating the result with respect to the wave number k. The result of this operation is as follows.

$$I_i\int = I^*_c(k) w_i(k) dk = \sqrt{2\pi} \cdot \sigma_w \cdot (I_r + I_s) + 2\sqrt{rI^*_r I_o} \exp(-2\sigma_w^2 z_0^2) \cos(2k_i z_0) \qquad (16)$$

As shown by the second term on the right side of Equation (16), the amplitude $(r \times I_r \times I_o)^{1/2} \cos(2k_i z_0)$ of the interference light is multiplied by $\exp(-2\sigma_w^2 \times z_0^2)$ by the optical demultiplexer 63.

This factor $\exp(-2\sigma_w^2 \times z_0^2)$ decreases rapidly as $z_0$ increases. Hence, as $z_0$ increases, the amplitude of the interference light outputted from the optical demultiplexer 63 decreases rapidly.

Here, $\exp(-2\sigma_w^2 \times z_0^2)$ is 1 when the position $z_0$ of the measurement object (mirror) is zero. On the other hand, when $z_0$ becomes $(\ln 2/2)^{1/2}/\sigma_w$, $\exp(-2\sigma_w^2 \times z_0^2)$ becomes $\frac{1}{2}$.

Therefore, $(\ln 2/2)^{1/2}/\sigma_w$ may be considered as the effective coherence length of the reference light and signal light in this embodiment.

The half width at half maximum $(2 \times \ln 2)^{1/2} \times \sigma_w$ of the transmittance function of the optical demultiplexer, expressed in Equation (15), may be adjusted by varying the structure of the AWG constituting the optical demultiplexer.

Accordingly, the effective coherence length $(\ln 2/2)^{1/2}/\sigma_w$ may also be adjusted.

Figure 4:
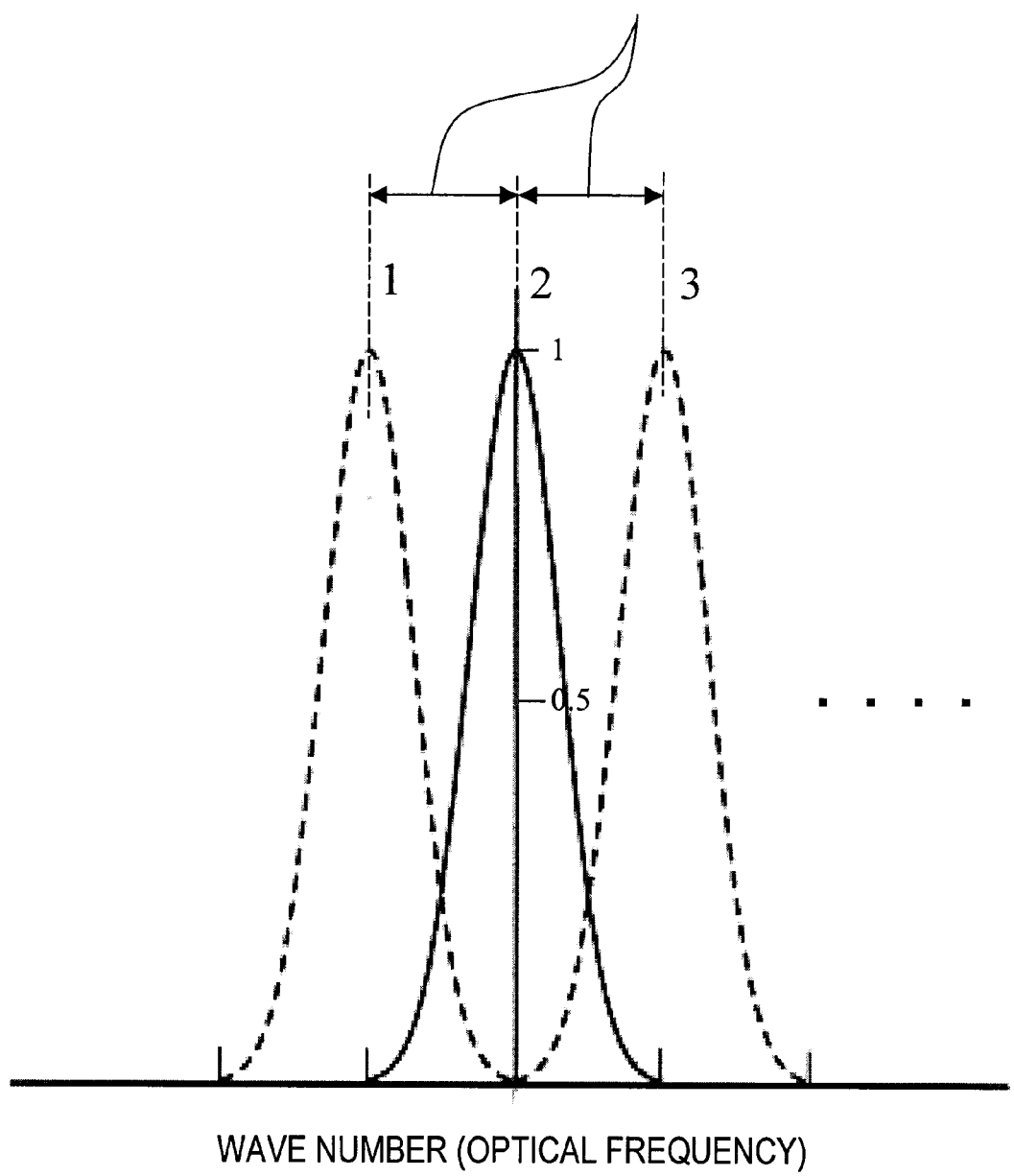
FIG. 4 shows a transmittance characteristic of an optical demultiplexer according to a third embodiment.

For example, it is assumed that the channel spacing is $\Delta k$, and the half width at half maximum $(2 \times \ln 2)^{1/2} \times \sigma_w$ of the transmittance function is $\Delta k/3$, as shown in FIG. 4 (the full width at half maximum is $2\Delta k/3$). In this case, the effective coherence length is $3 \times \ln 2/\Delta k$.

In this embodiment, the wave number spacing is 10 GHz when the wave number is converted to frequency. Therefore, the maximum ranging depth is 7.5 mm, as derived from Equation (3). Meanwhile, the coherence length $3 \times \ln 2/\Delta k$ is 9.9 mm. Note that $\Delta k$ ($= 2\pi \Delta f/c$; where $\Delta f$ is the frequency interval and c is the speed of light) is $2.095 \times 10^{-4}$ μm$^{-1}$.

In other words, in this embodiment, the effective coherence length (9.9 mm) is greater than the maximum ranging depth (7.5 mm). Therefore, the amplitude of the intensity $I_i$ of the interference light at the maximum ranging depth never falls to or below 1/2 (−3 db) the amplitude at $z_0=0$ mm.

Figure 5:
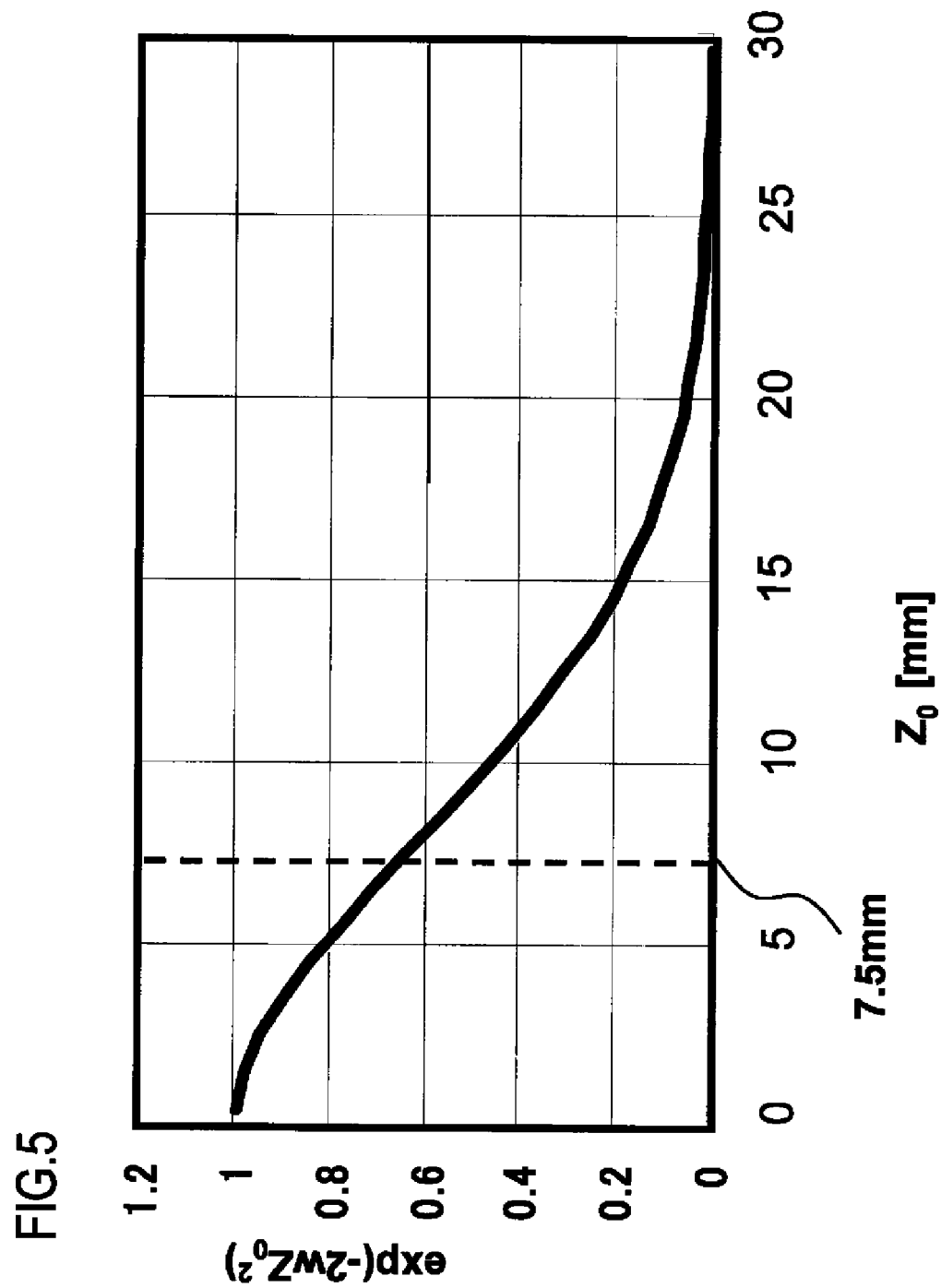
FIG. 5 is a view showing a relationship between a mirror position $z_0$ and an interference light intensity decrease factor $\exp(-2\sigma_w^2 \times z_0^2)$, according to the third embodiment.

To estimate the degree to which the amplitude of the interference light actually decreases in the maximum ranging depth (7.5 mm), $\exp(-2\sigma_w^2 \times z_0^2)$ may be calculated with $z_0=7.5$ mm. The result is 0.673. In other words, the amplitude of the intensity $I_i$ of the interference light in the maximum ranging depth is 0.673 times the amplitude at $z_0=0$ mm. FIG. 5 shows the relationship between the mirror position $z_0$ and the interference light intensity decrease factor $\exp(-2\sigma_w^2 \times z_0^2)$.

Hence, the intensity of the OCT signal is 0.45 times (=0.673$^2$; −3.4 dB) the OCT signal at $z_0=0$ mm. This reduction in the OCT signal has substantially no effect on tomographic image capturing. Therefore, the depth range becomes equal to the maximum ranging depth.

In other words, the coherence length is virtually increased, and therefore the amplitude of the interference light exhibits substantially no decrease even in the maximum ranging depth. Hence, according to this embodiment, the depth range is expanded to the maximum ranging depth.

In a typical measurement environment, substantially no objects other than the measurement object enter the range of the effective coherence length, i.e. 9.9 mm. Therefore, a situation does not occur in which an object other than the measurement object, for example reflection light from the focusing lens 8, interferes with the reference light so as to raise the noise level of the OCT signal. In other words, according to this embodiment, noise level does not increase due to reflection light from an object other than the measurement object. Hence, according to this embodiment, interference noise that impedes expansion of the OCT measurement range does not occur.

Figure 6:
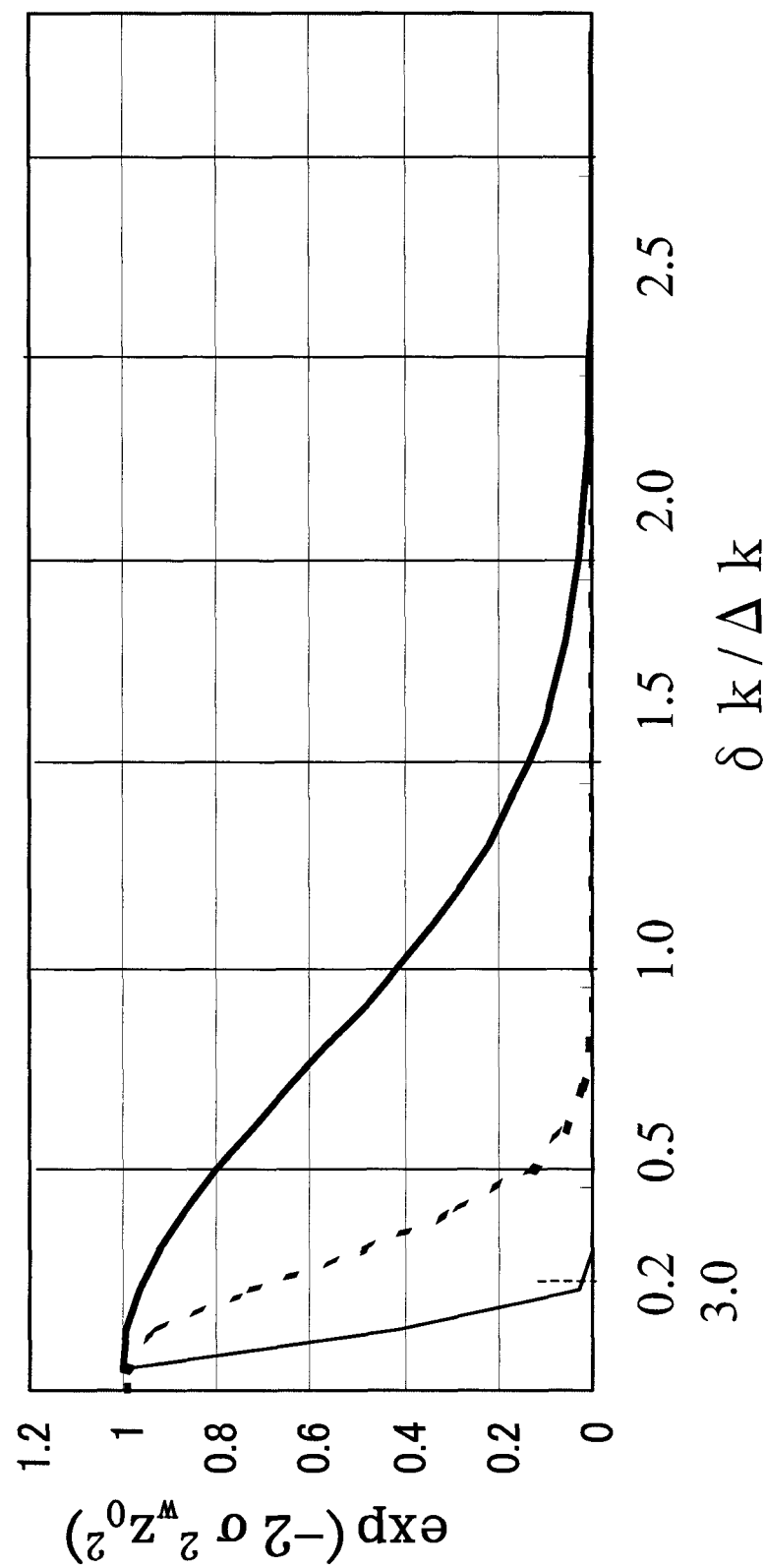
FIG. 6 is a view showing a relationship between a full width at half maximum of the transmittance characteristic of the optical demultiplexer and the interference light intensity decrease factor $\exp(-2\sigma_w^2 \times z_0^2)$, according to the third embodiment.

FIG. 6 shows the interference light amplitude decrease factor $\exp(-2\sigma_w^2 \times z_0^2)$ relative to the full width at half maximum $\delta k$ of the transmittance characteristic of the channels in the optical demultiplexer 63. The abscissa shows a value obtained by normalizing the full width at half maximum $\delta k$ of the transmittance characteristic by the channel wave number spacing $\Delta k$ (i.e. the channel wave number width). The ordinate shows $\exp(-2\sigma_w^2 \times z_0^2)$.

The thick solid line shows a case in which $z_0$ is equal to the maximum ranging depth. The broken line shows a case in which $z_0$ is equal to three times the maximum ranging depth. The narrow solid line shows a case in which $z_0$ is equal to ten times the maximum ranging depth.

A preferred range for the full width at half maximum $\delta k$ of the transmittance characteristic of the channels will be investigated on the basis of this drawing.

The thick solid line is used to estimate the degree to which interference light produced by signal light attenuates when $z_0$ is in the maximum ranging depth.

The narrow solid line is used to estimate the magnitude of the interference noise.

The object located closest to the measurement object is the focusing lens 8. The focusing lens 8 may be disposed in a position away from the measurement object by at least 10 times the maximum ranging depth. For example, when measuring the anterior eye portion, the focusing lens may be disposed in a position away from the eye by at least 7.5 cm in relation to the maximum ranging depth of 7.5 mm. The narrow solid line in FIG. 6 is used to estimate the intensity of the reflection light from the focusing lens when the focusing lens is disposed in this position.

As is evident from the thick solid line in FIG. 6, when the full width at half maximum k of the transmittance characteristic is smaller than the channel spacing $\Delta k$ of the optical demultiplexer (when the value on the abscissa is smaller than 1), the amplitude of the interference light intensity (to be referred to as the "interference light amplitude" hereafter) in the maximum ranging depth is at least 0.41 times the amplitude of the interference light occurring when the full width at half maximum $\delta k$ of the transmittance characteristic is zero. This degree of interference light attenuation may be ignored.

Meanwhile, as is evident from the narrow solid line, when the full width at half maximum $\delta k$ of the transmittance characteristic is greater than 0.2 times of the channel spacing $\Delta k$ (when the value on the abscissa is greater than 0.2), the interference light amplitude from a reflective surface existing at a remove of 10 times the maximum ranging depth is no more than 0.028 times the amplitude of interference light occurring when the full width at half maximum $\delta k$ of the transmittance characteristic is zero (the value on the abscissa is zero). When the interference light amplitude decreases to this point, interference noise can be ignored.

Hence, the full width at half maximum $\delta k$ of the transmittance characteristic is preferably narrower than the channel spacing $\Delta k$ and greater than 0.2 times the channel spacing $\Delta k$. More preferably, the full width at half maximum $\delta k$ of the transmittance characteristic is narrower than 0.85 times the channel spacing $\Delta k$ (so that the interference light amplitude is 0.57) and greater than 0.35 times the channel spacing $\Delta k$ (so that the interference light amplitude is 0.0003). Even more preferably, the full width at half maximum $\delta k$ of the transmittance characteristic is narrower than 0.7 times the channel spacing $\Delta k$ (such that the interference light amplitude is $2.2 \times 10^{-10}$) and greater than 0.5 times the channel spacing $\Delta k$.

Fourth Embodiment

This embodiment relates to an optical coherence tomography apparatus that uses an optical filter to restore the signal-to-noise ratio, which is decreased through use of the optical demultiplexer.

(1) Principle

The signal to noise ratio (S/N ratio) of FD-OCT is expressed by the following equation (S. H. Yun, G. J. Tearney, J. F. de Boer, N. Iftimia, and B. E. Bouma, "High-speed optical frequency-domian imaging", *OPTICS EXPRESS*, Vol. 11, p. 2953-2963, 2003.).

$$\frac{\eta P_s}{h v f_A} \quad (17)$$

Here, $\eta$ is the sensitivity of the photo-detecting device. $P_s$ is the optical intensity of a signal light received by the photo-detecting device. The photon energy is denoted by hv. The A-line scan rate is denoted by $f_A$. As is evident from Equation (17), the S/N ratio of FD-OCT is proportional to the optical intensity of the signal light. Hence, to increase the sensitivity of FD-OCT by raising the S/N ratio, it is important to increase the intensity of the signal light. Equation (17) is also applicable to the OCT (OD-OCT) of the present invention.

Figure 7:
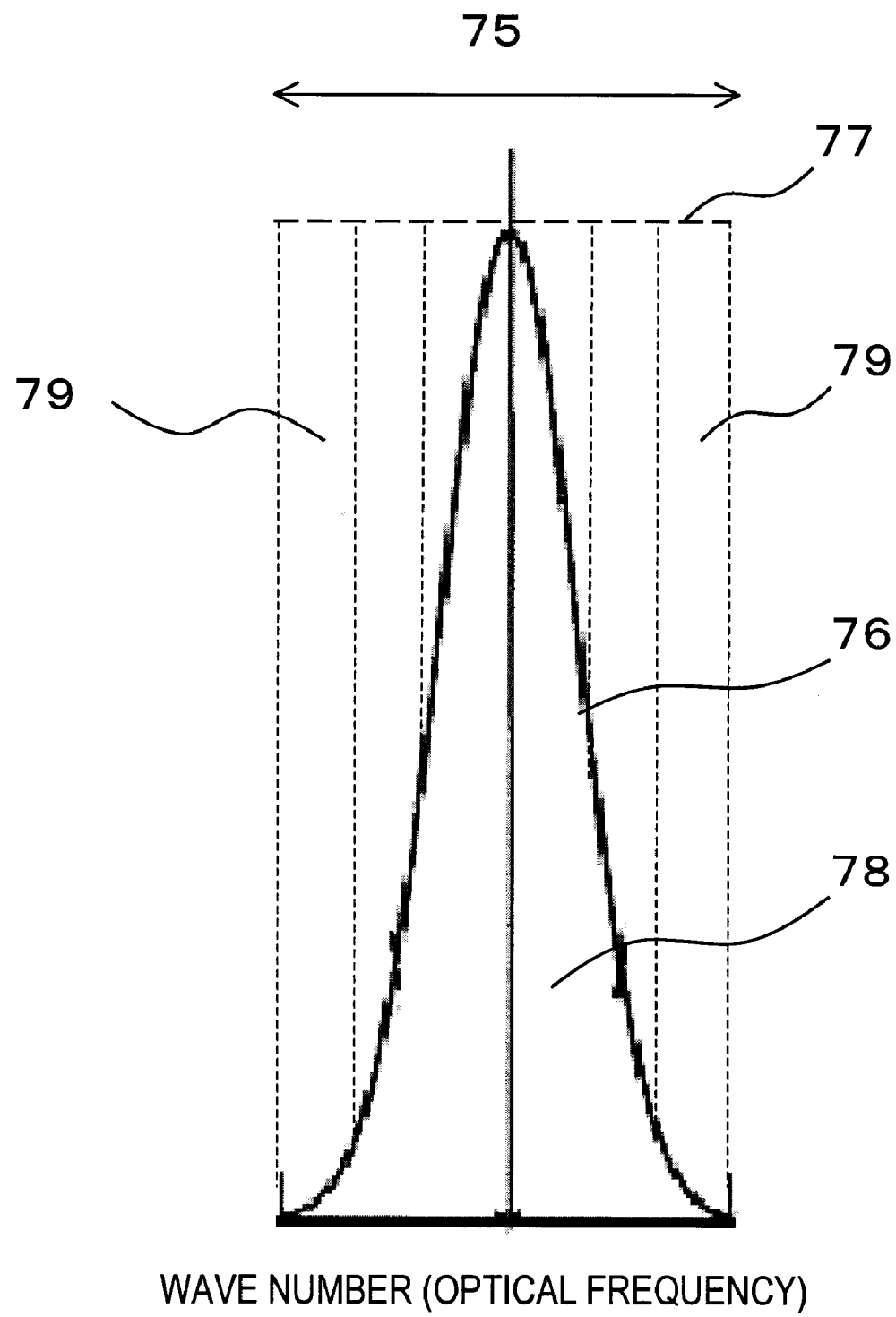
FIG. 7 is a view illustrating a relationship between the transmission characteristic of one channel of the optical demultiplexer and the spectrum of interference light incident on the optical demultiplexer.

FIG. 7 shows a transmittance characteristic 76 in a single channel 75 of the optical demultiplexer 63 and a spectrum 77 of interference light incident on the optical demultiplexer 63. The part on an inside 78 of the transmittance characteristic 76 is the only light that reaches the photo-detecting devices 64 in the spectrum 77 of the interference light. A remaining part 79 is lost when passing through the optical demultiplexer 63, and does not reach the photo-detecting devices 64.

In other words, only a part of the signal light generated by the measurement object reaches the photo-detecting devices 64. Therefore, as is evident from Equation (17), the signal to noise ratio (SN ratio) is decreased in the OCT (OD-OCT) of the present invention.

For example, the full width at half maximum of the transmittance of a single channel of the optical demultiplexer 63 is assumed to be ⅓ of the wave number spacing of the channels. Then, the S/N ratio decreases by substantially −5 dB. When the full width at half maximum of the transmittance is ⅕ of the wave number spacing of the channels, the S/N ratio decreases by substantially −7 dB. When the full width at half maximum of the transmittance is 1/10 of the wave number spacing of the channels, the S/N ratio decreases by substantially −10 dB.

These decreases in the S/N ratio cannot be ignored. Hence, in this embodiment, such decreases in the S/N ratio are prevented in the following manner.

The simplest method of improving the S/N ratio is to increase the intensity of the measurement light. However, if the measurement light becomes too intense, the human body may be damaged. Therefore, there is an upper limit to the optical intensity with which the human body can be irradiated. Accordingly, there is a limit to the degree with which the SN ratio can be increased by intensifying the measurement light.

Figure 8:
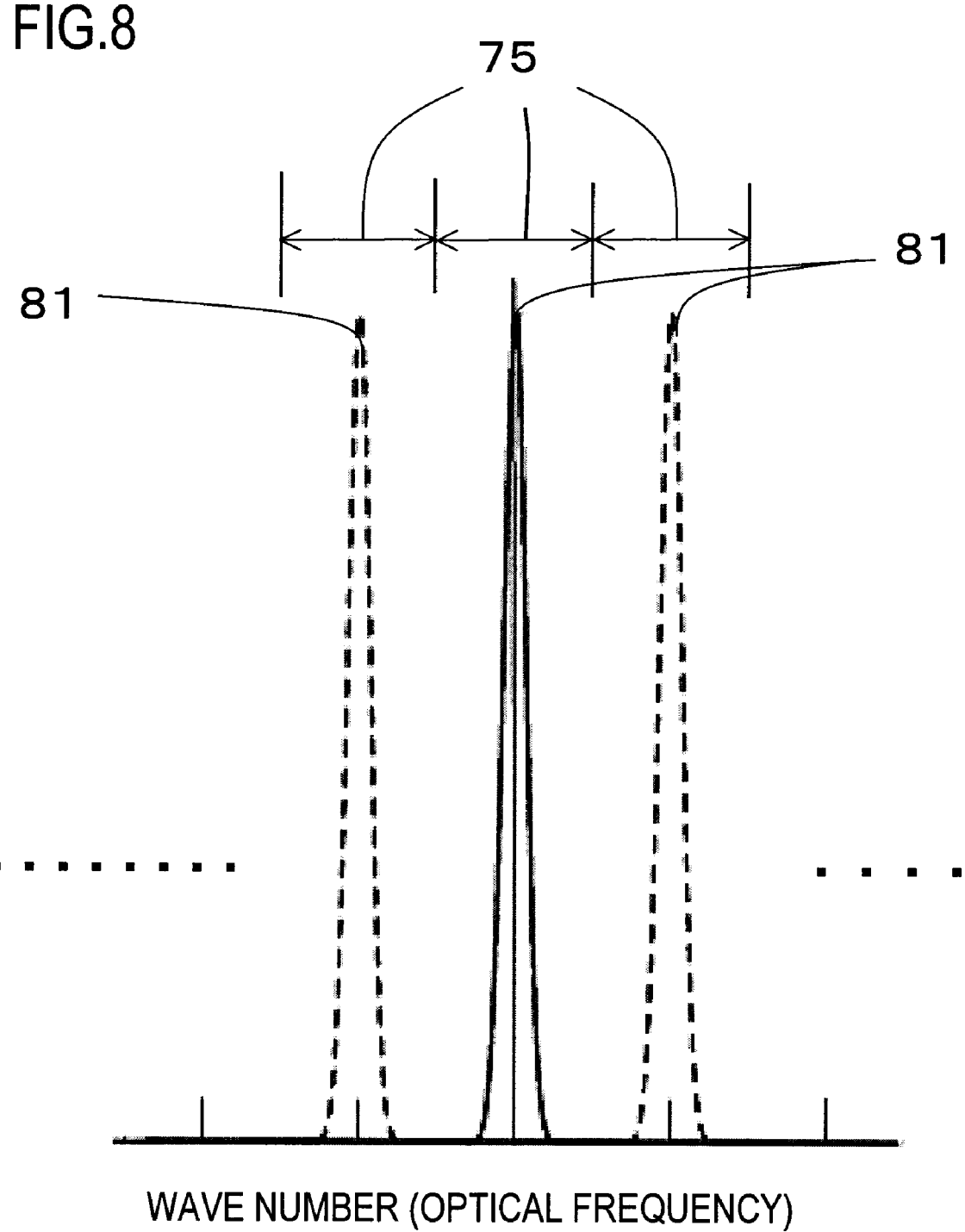
FIG. 8 shows a spectrum of output light from an optical filter according to a fourth embodiment.

In this embodiment, the output light of the broadband light generating device is shaped by an optical filter such that the optical intensity at either end of the channels (wave number sections) of the optical demultiplexer 63 becomes smaller than the optical intensity in the center of the channels (wave number sections). In so doing, a spectrum such as that shown in FIG. 8 is obtained. Light having a spectrum shaped into this comb tooth shape enters the first coupler (optical divider) 52, and the measurement light and reference light are generated therefrom.

The optical coherence tomography apparatus according to this embodiment has an optical filter 78 that shapes the output light of the broadband light generating device 1 such that the optical intensity at the both ends of each of predetermined wave number sections (channels) becomes smaller than the optical intensity in the center of each of the predetermined wave number sections, and outputs the shaped output light to the optical divider 52.

Hence, the spectrum of the interference light generated by the second coupler (optical divider) 54 also takes the form shown in FIG. 8. As a result, even when the interference light is spectrally divided by the optical demultiplexer having the transmission characteristic shown in FIG. 4, no loss occurs in the signal light. Accordingly, the S/N ratio does not decrease.

Note that FIG. 8 shows the output light of the optical filter 78 in relation to a wave number (optical frequency) corresponding to three of the channels in the optical demultiplexer 63.

(3) Apparatus Constitution

First, the constitution of the optical coherence tomography apparatus according to this embodiment will be described.

Figure 10:
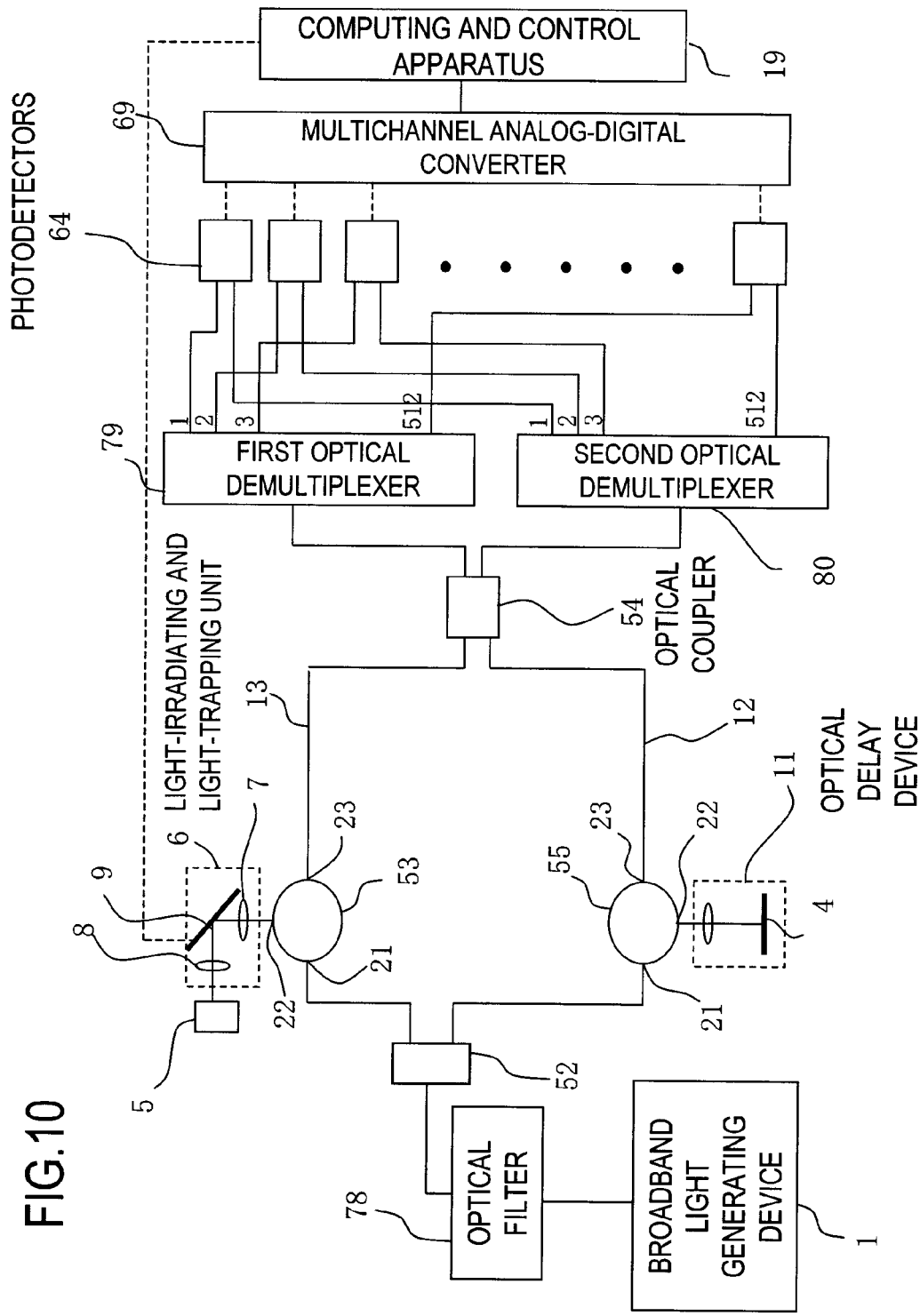
FIG. 10 is a block diagram showing the main parts of an optical coherence tomography apparatus according to the fourth embodiment.

As shown in FIG. 10, the OCT apparatus of this embodiment has a broadband light generating device 1 composed of a super luminescent diode (SLD). A light output port of the broadband light generating device 1 is optically connected to a light input port of the optical filter 78, which is composed of a Fabry-Perot etalon. A light output port of the optical filter 78 is optically connected to a light input port of a first coupler 52 (optical divider), which is composed of a directional coupler for dividing light into two (at 10:90, for example).

A first light output port (on the 90% divided proportion side) of the first coupler 52 is optically connected to a light input port 21 of a first optical circulator 53. A light-output and light-input port 22 of the optical circulator 53 is connected to a first light-irradiating and light-trapping unit 6 for irradiating a measurement object 5 with measurement light and trapping signal light reflected by the measurement object 5. A light output port 23 of the optical circulator 53 is connected to a first light input port of a second coupler 54 (optical coupler), which is composed of a directional coupler (with a division ratio of 50:50).

The light-irradiating and light-trapping unit 6 has a collimator lens 7 for shaping the measurement light outputted from the light-output and light-input port of the optical circulator 53 into parallel beams, a focusing lens 8 for converging the parallel beams on the measurement object 5, and a galvanometer mirror 9 for scanning the surface of the measurement object 5 with the measurement light in a linear fashion by deflecting the measurement light.

A second light output port (on the 10% divided proportion side) of the first coupler 52 is optically connected to the light input port 21 of an optical circulator 55. The light-output and light-input port 22 of the optical circulator 55 is optically connected to an optical delay device 11 for delaying the reference light outputted from an optical fiber end portion by causing the reference light to go from the optical fiber end portion to a reference mirror 4 and back. The reference mirror 4 is supported by a support so as to be capable of moving forward and backward, and the position thereof is adjusted such that the optical path lengths of a reference arm 12 and a sample arm 13 are substantially equal.

A light output port 23 of the optical circulator 55 is optically connected to a second light input port of the second coupler 54, which is composed of a directional coupler (with a division ratio of 50:50). A first light output port of the second coupler 54 is optically connected to a light input port of a first optical demultiplexer 79, which is composed of an AWG (arrayed-waveguide grating).

The plurality of light output ports of the first optical demultiplexer 79 are connected to first light input ports of a plurality of photo-detecting devices 64 for subjecting first optical signals incident on the first light input ports to photoelectric conversion to generate first electric signals, subjecting second optical signals incident on second light input ports to photoelectric conversion to generate second electric signals, detecting a difference between the first electric signals and second electric signals, and outputting the electric signals.

A second light output port of the second coupler 54 is optically connected to a light input port of a second optical demultiplexer 80 composed of an AWG (arrayed-waveguide grating).

The first and second optical demultiplexers 79, 80 are structured identically. Hence, the spectral characteristic, or in other words the channel spacing (i.e. the channel width) and the full width at half maximum of the transmission characteristic are identical in the first and second optical demultiplexers 79, 80.

A plurality of light output ports of the second optical demultiplexer 80 are connected to the second light input ports of the plurality of photo-detecting devices 64 for subjecting the first optical signals incident on the first light input ports to photoelectric conversion to generate the first electric signals, subjecting the second optical signals incident on the second light input ports to photoelectric conversion to generate the second electric signals, detecting the difference between the first electric signals and second electric signals, and outputting the electric signals. Here, the channel numbers of the first and second optical demultiplexers 79, 80 connected to the respective optical detectors are identical. In other words, the center wavelengths of the two sets of channels coincide together.

Output terminals of the photo-detecting devices 64 are connected individually to input terminals (channels) of a multichannel analog to digital converter 69. An output terminal of the multichannel analog to digital converter 69 is electrically connected to an input terminal of a computing and control apparatus 19 for calculating a reflectivity profile. An output portion of the computing and control apparatus 19 is electrically connected to an input portion of a display apparatus (not shown) such as a monitor or printer for displaying calculation results. The computing and control apparatus 19 controls the galvanometer mirror 9 of the light-irradiating and light-trapping unit 6 on the basis of input information.

The center wavelength of the broadband light generating device 1 is 1550 nm, and the full width at half maximum thereof is 50 nm. Further, the intensity of the output light of the broadband light generating device 1 is greater than that used when the optical filter 78 is not present (i.e. the first embodiment). The reason for this is that the optical intensity (a value obtained by integrating the optical intensity spectra with respect to the wave number) of the output light from the optical filter 78 is made coincident with the intensity of the light outputted by the broadband light generating device 1 when the optical filter is not used.

The half-width of the optical filter 78 composed of a Fabry-Perot etalon is 1.36 GHz.

Further, the number of channels in the AWG, or in other words the number of light output ports, is 512. A wave number spacing 75 of the channels is 10 GHz. A full width at half maximum 68 of the transmittance of each channel is identical to that of the second embodiment, i.e. 6.7 GHz (=10 GHz×2/3).

The response speed of the photo-detecting devices 64 is 0.1 ns. As described above, a pair of input terminals of each photo-detecting device 64 is connected to each output port of the first and second AWGs. Each of the output terminals of the photo-detecting devices 64 is connected to each of the input terminals of the multichannel analog to digital converter 69 having 512 input terminals.

The sampling frequency of the multichannel analog to digital converter 69 is 60 MHz. In other words, the sampling time is 16.7 ns. The multichannel analog to digital converter 69 subjects an electric signal inputted from each input terminal to analog/digital conversion within this sampling time, and records the resulting digital signals in a built-in recording apparatus. The digital signals recorded in the recording apparatus are output in sequence to the computing and control apparatus 19.

In this embodiment, the optical filter 78 is composed of a Fabry-Perot etalon.

Incidentally, a transmittance $f_{FP}$ of a Fabry-Perot etalon is expressed by the following equation.

$$f_{FP} = \frac{(1-R)^2}{1+R^2 - 2R\cos(2nkl\cos\theta)} \quad (18)$$

Here, l is the interval between two reflection mirrors constituting a Fabry-Perot interferometer. R is the reflectivity of the reflection mirrors. The refractive index of a substance sandwiched between the reflection mirrors is denoted by n. The wave number of light incident on the Fabry-Perot interferometer is denoted by k. θ is the angle formed between the light incident on the Fabry-Perot interferometer and the normal of the reflection mirrors.

In the Fabry-Perot interferometer of this embodiment, l=15.0 mm, R=0.79, n=1 (the refractive index of air), and θ=0.

The full width at half maximum of Equation (18) is expressed by the following equation.

$$\frac{2\arcsin(1/\sqrt{F})}{nl\cos\theta} \quad (19)$$

Here, F is expressed by the following equation.

$$F = \frac{4R}{(1-R)^2} \quad (20)$$

By inserting l=15.0 mm, R=0.79, n=1, and θ=0 into this equation, the full width at half maximum of the optical filter 78 in a wave number, which corresponds to 1.36 GHz, is obtained.

A Mach-Zehnder interferometer may be used as the optical filter 78.

The transmission characteristic of a Mach-Zehnder interferometer is expressed by the following equation.

$$f_{MZ} = \sum_i \left\{ \frac{1}{2} + \frac{1}{2}\cos\left[\frac{2\pi}{\Delta k}(k - k_i)\right] \right\} \quad (21)$$

Here, $k_i$ is each center wave number, and $\Delta k$ is the recurrence period relative to the wave number.

As is evident from this equation, the full width at half maximum of a Mach-Zehnder interferometer is ½ of the recurrence period $\Delta k$ (the half width at half maximum is ¼ of $\Delta k$).

Figure 9:
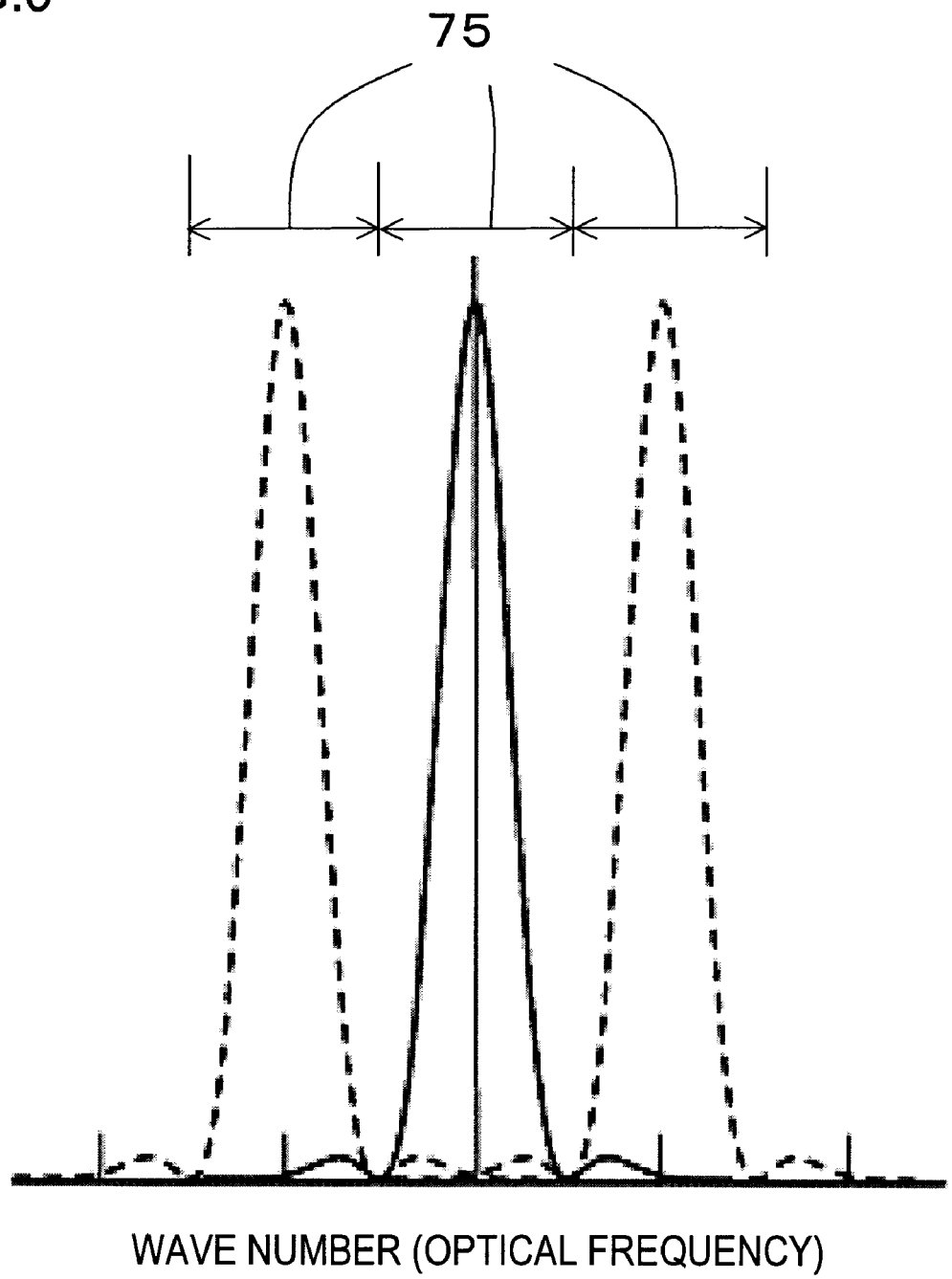
FIG. 9 shows a spectrum of output light from an optical filter composed of a Mac-Zender interferometer.

FIG. 9 is a spectrum of the output light when a Mach-Zehnder interferometer is used as the optical filter. The recurrence period $\Delta k$ is set to coincide with the width of the channel 75 of the optical demultiplexer.

(4) Operation

Next, an operation of the optical coherence tomography apparatus according to this embodiment will be described.

Broadband light outputted from the broadband light generating device 1 is shaped into a comb-shaped spectrum by the optical filter 78 (output light having the spectrum shown in FIG. 8 is outputted from the optical filter 78).

The spacing of each peak 81 of the comb-shaped spectrum coincides with the channel spacing, or in other words the channel width, of the optical demultiplexers 79, 80. Furthermore, the center wave number of each peak 81 coincides with the center wave number of each channel of the optical demultiplexers 79, 80. In other words, the optical filter 78 shapes the broadband light such that the optical intensity of the output light from the broadband light generating device 1 at a wave number corresponding to the both ends of each channel 75 of the optical demultiplexers 79, 80 becomes smaller than the optical intensity at a wave number corresponding to the center of each channel.

The broadband light shaped by the optical filter 78 is divided into two in a proportion of 10:90 by the first coupler 52 (optical divider). One part of the divided light (measurement light) is led to the light-irradiating and light-trapping unit 6 by the first optical circulator 53.

The measurement light incident on the light-irradiating and light-trapping unit 6 is emitted onto the measurement object 5 by the light-irradiating and light-trapping unit 6. The measurement light emitted onto the measurement object 5 is reflected by the surface and interior of the measurement object 5. A part of the reflected light is captured by the light-irradiating and light-trapping unit 6 to form signal light.

The signal light is led to the first light input port of the second coupler 54 (optical coupler) by the first optical circulator 53.

The other part of the light divided by the optical divider 52 (reference light) is led to the optical delay device 11 by the optical circulator 55. The reference light is caused to travel a predetermined optical path length in the optical delay device 11, and is then led to the second light input port of the second coupler 54 (optical coupler) by the second optical circulator 55.

The signal light and reference light are combined by the second coupler 54 (optical coupler) to form interference light. Interference light that is outputted from the first light output port of the second coupler 54 (optical coupler) is led to the input port of the first optical demultiplexer 79. Meanwhile, interference light that is outputted from the second output port of the second coupler 54 (optical coupler) is led to the input port of the second demultiplexer 80.

As noted above, the interval between each peak 81 constituting the spectrum of the output light outputted from the optical filter 78 coincides with the channel spacing of the optical demultiplexers 79, 80. Moreover, the center wave number of each peak 81 coincides with the center wave number of each channel of the optical demultiplexers 79, 80.

Therefore, the interference light incident on the optical demultiplexers 79, 80 is separated into light having a spectrum that corresponds to each of the spectrum peaks 81 shown in FIG. 8 by the optical demultiplexers 79, 80. In other words, the interference light is spectrally divided by the optical demultiplexers 79, 80. Each of the spectrally divided interference light is outputted from the individual light output ports of the optical demultiplexers 79, 80.

The interference light outputted individually from the light output ports of the first and second optical demultiplexers 79, 80 respectively enters the first and second light input ports of the photo-detecting devices 64 that are optically connected to the light output ports.

The individual photo-detecting devices 64 subject the first optical signals incident on the first light input ports to photoelectric conversion to generate the first electric signals, subject the second optical signals incident on the second light input ports to photoelectric conversion to generate the second electric signals, detect the difference between the first electric signals and second electric signals, and output the electric signals.

Here, the difference between the first electric signal and second electric signal is proportional to the equation $2(r\, I_r\, I_o)^{1/2} \exp(-2\sigma_w^2\, z_0^2)$ on the right side of Equation (16), or in other words the amplitude of the interference light. This is based on the properties of the second coupler, which is composed of a directional coupler.

The electric signals outputted from each optical photo-detecting devices 64 are inputted into each input terminal of the multichannel analog to digital converter.

The electric signals inputted into the respective input terminals of the multichannel analog to digital converter 69 are converted into digital signals. The digital signals are recorded in the built-in recording apparatus of the multichannel analog to digital converter 69. The digital signals recorded in the recording apparatus are outputted from the multichannel analog to digital converter 69 in sequence. The digital signals outputted from the multichannel analog to digital converter 69 are inputted into the computing and control apparatus 19. The computing and control apparatus 19 calculates a reflectivity profile on the basis of the input digital signals. The operation of the computing and control apparatus 19 is identical to that of the computing and control apparatus 19 of the first embodiment.

Here, the full width at half maximum δk of the spectrum of the interference light is 0.136 times (=1.36 GHz/10 GHz) the wave number spacing Δk of each channel of the optical demultiplexers 79, 80. Meanwhile, the full width at half maximum of the transmittance of each channel of the optical demultiplexers 79, 80 is 0.666 times (=⅔) the wave number spacing Δk of the channel. In other words, the full width at half maximum δk of the spectrum of the interference light is considerably narrower than the full width at half maximum of the transmittance of each channel of the optical demultiplexers 79, 80.

Therefore, the interference light undergoes substantially no attenuation even after passing through the optical demultiplexers 79, 80. In other words, the intensity of the signal light received by the photo-detecting devices 64 undergoes substantially no loss in the optical demultiplexers 79, 80.

Hence, the S/N ratio of the electric signal outputted by the photo-detecting device 64 is greatly improved over that of a case in which the optical filter 78 is not used. Accordingly, the SN ratio of the reflectivity profile calculated by the computing and control apparatus 19 is also improved.

(5) Enlargement of Coherence Length

According to this embodiment, in addition to the effect of improving the S/N ratio of the OCT signal as described above, an effect of enlarging the effective coherence length of the signal light and reference light is also obtained.

As described above, the transmittance of the $i^{th}$ channel of the optical demultiplexer is provided by the following equation (K. Okamoto "Fundamentals of Optical Waveguides", Academic Press, Amsterdam (2006) pp. 417-534.).

$$w_i(k) = \exp\left[-\frac{(k-k_i)^2}{2\sigma_w^2}\right] \quad (15)$$

Here, $k_i$ is the center wave number of the $i^{th}$ channel.

In this embodiment, the broadband light incident on the optical demultiplexer is subjected to spectrum shaping by the optical filter 78. Hence, the spectrum of the light outputted from each channel of the optical demultiplexer is obtained by multiplying a substantially flat broadband light spectrum by the following function, rather than Equation (15).

$$w_i^*(k) = \exp\left[-\frac{(k-k_i)}{2\sigma_{sum}^2}\right] \quad (22)$$

Here, $$\sigma_{sum}^2 = \frac{\sigma_s^2 \sigma_w^2}{\sigma_s^2 + \sigma_w^2} \quad (23)$$

$\sigma_s$ is a parameter in a case where the transmission characteristic of the optical filter 78 is approximated by the following equation in a section corresponding to the $i^{th}$ channel of the optical demultiplexer.

$$\exp\left[-\frac{(k-k_i)}{2\sigma_s^2}\right] \quad (24)$$

Hence, the effective coherence length $l_c$ in this embodiment is expressed by the following equation.

$$l_c = \sqrt{\frac{\ln 2}{2}} \frac{1}{\sigma_{sum}} \quad (25)$$

As is evident from Equation (23), $\sigma_{sum}$ is smaller than $\sigma_w$. Hence, when the spectrum of the output light of the broadband light generating device 1 is shaped by the optical filter 78, the coherence length $l_c$ increases in length.

The half width at half maximum of the transmittance function of the optical demultiplexer may be adjusted by varying the structure (dimensions and so on) thereof. However, there is a limit to the adjustable range. If there is a need to extend the effective coherence length $l_c$ beyond this range, the effective coherence length $l_c$ can be extended further using the optical filter.

In the optical filter 78 of this embodiment, $(2 \ln 2)^{1/2} \sigma_s = 1/14.7 \times \Delta k$. Here, Δk is the channel spacing of the optical demultiplexer. Further, $\Delta k = 2.095 \times 10^{-4}\,\mu m^{-1}$ (10 GHz).

Meanwhile, $(2 \ln 2)^{1/2} \sigma_w = \frac{1}{3} \times \Delta k$. Accordingly, $(2 \ln 2)^{1/2} \sigma_{sum} = \frac{1}{15} \times \Delta k$.

Hence, according to Equation (25), the effective coherence length $l_c$ is 49.6 mm.

On the other hand, when a Mach-Zehnder interferometer is used as the optical filter, $(2 \ln 2)^{1/2} \sigma_s = \frac{1}{4} \times \Delta k$. Accordingly, $(2 \ln 2)^{1/2} \sigma_{sum} = \frac{1}{5} \times \Delta k$. Therefore, the effective coherence length $l_c$ is 16.5 mm.

In either case, the effective coherence length $l_c$ is longer than the effective coherence length 9.93 mm of a case in which an optical filter is not used.

Fifth Embodiment

This embodiment relates to an optical coherence tomography apparatus in which an optical amplifier 82 is used to amplify the signal light, so that the S/N ratio, or in other words the sensitivity, is increased.

Figure 11:
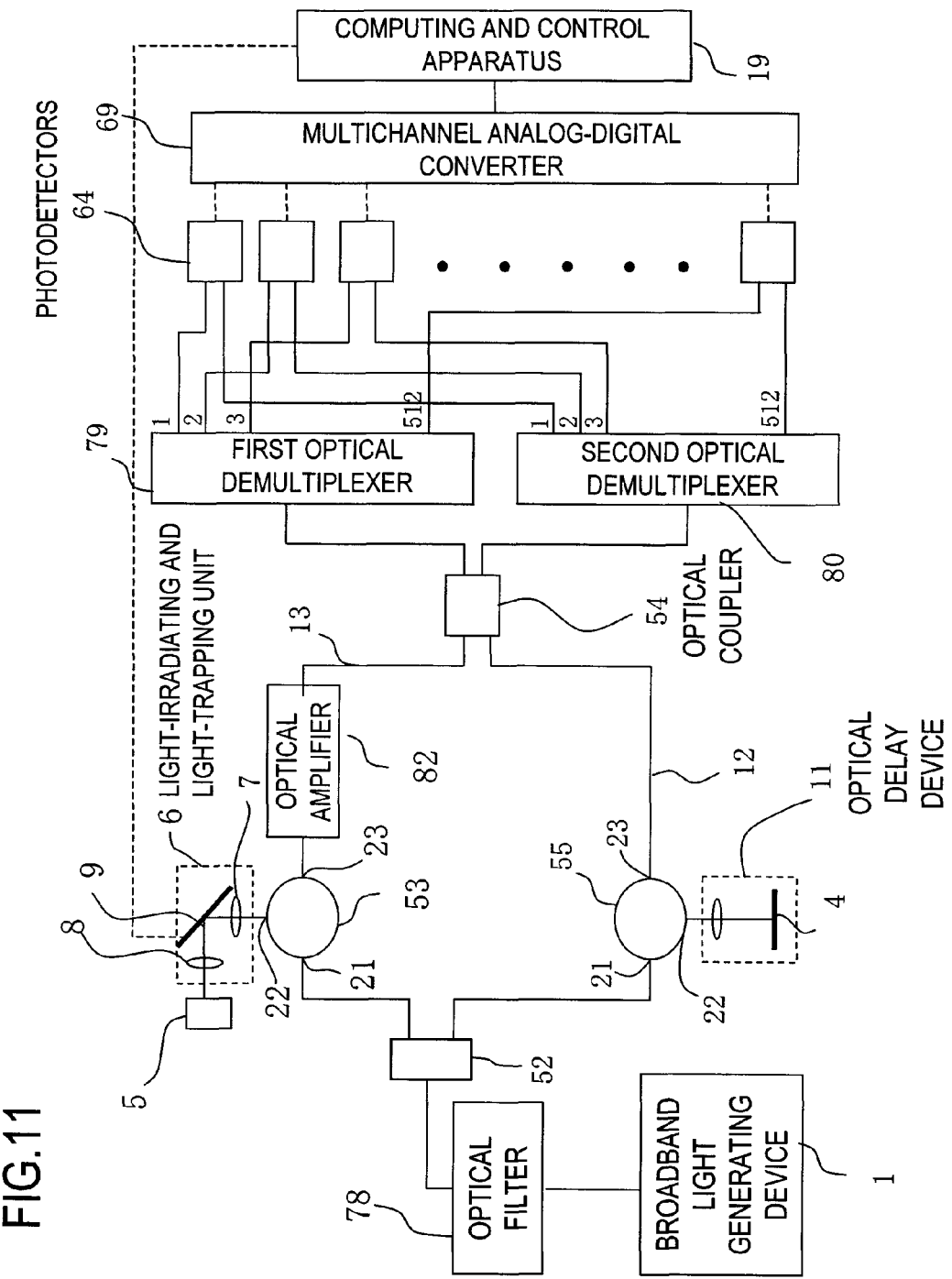
FIG. 11 is a block diagram showing the main parts of an optical coherence tomography apparatus according to a fifth embodiment.

FIG. 11 shows the constitution of the optical coherence tomography apparatus according to this embodiment. This optical coherence tomography apparatus differs from the optical coherence tomography apparatus of the fourth embodiment in that an optical amplifier 82 composed of a semiconductor optical amplifier is disposed between the first circulator 53 and the optical coupler 54.

More specifically, a light input port of the optical amplifier 82, in place of the light input port of the optical coupler 54, is optically connected to the light output port of the light-irradiating and light-trapping unit 6. Further, a light output port of the optical amplifier 82, in place of the light output port 23 of the first optical circulator 53, is optically connected to a first input port of the optical coupler 54.

The optical amplifier 82 amplifies signal light incident on the light input port thereof, and outputs the amplified signal light from the light output port thereof. As a result, the intensity of the signal light is increased. Hence, as can be seen from Equation (17) the S/N ratio increases.

Incidentally, in this embodiment the signal light is amplified 100 times (20 dB) by the optical amplifier 82. Therefore, the S/N ratio increases by 20 dB.

In all of the embodiments described above, the optical spectrum of the output light from the broadband light generating device 1 is held within the free spectrum range of the optical demultiplexer. However, when the optical spectrum of the output light from the broadband light generating device 1 protrudes from the free spectrum range of the optical demultiplexer, the protruding light turns into noise.

To remove this noise, the protruding light may be removed by disposing an optical band-pass filter between the broadband light generating device 1 and the optical divider 52 (or the optical filter 78).

In the embodiments described above, examples in which an AWG is used as the optical demultiplexer were provided. However, an optical demultiplexer employing a diffraction grating or a holographic grating may be used as the optical demultiplexer (K. Aoyama and J. Minowa, "*Low-loss optical demultiplexer for WDM systems in the 0.8-µm wavelength region*", Applied Optics, Vol. 18, pp. 2834-2836, 1979. D. D. Do, N. Kim, T. Y. Han, J. W. An, and K. Y. Lee, "Design of cascaded volume holographic gratings to increase the number of channels for an optical demultiplexer", *Applied Optics*, Vol. 45, pp. 8714-8721, 2006.). Various other structures may be proposed as the optical demultiplexer, and these optical demultiplexers may be used instead of an AWG.

Further, in the embodiment described above, the spectrum of the output light from the broadband light generating device 1 is shaped into a comb shape using the optical filter 78. However, the optical filter 78 may be omitted, and a light source that outputs light with a comb-shaped optical spectrum by nature, i.e. a comb optical generator, may be used instead of the broadband light generating device 1. Note, however, that the coherence length of a typical comb optical generator is too long, and therefore interference noise may occur.

Figure 12:
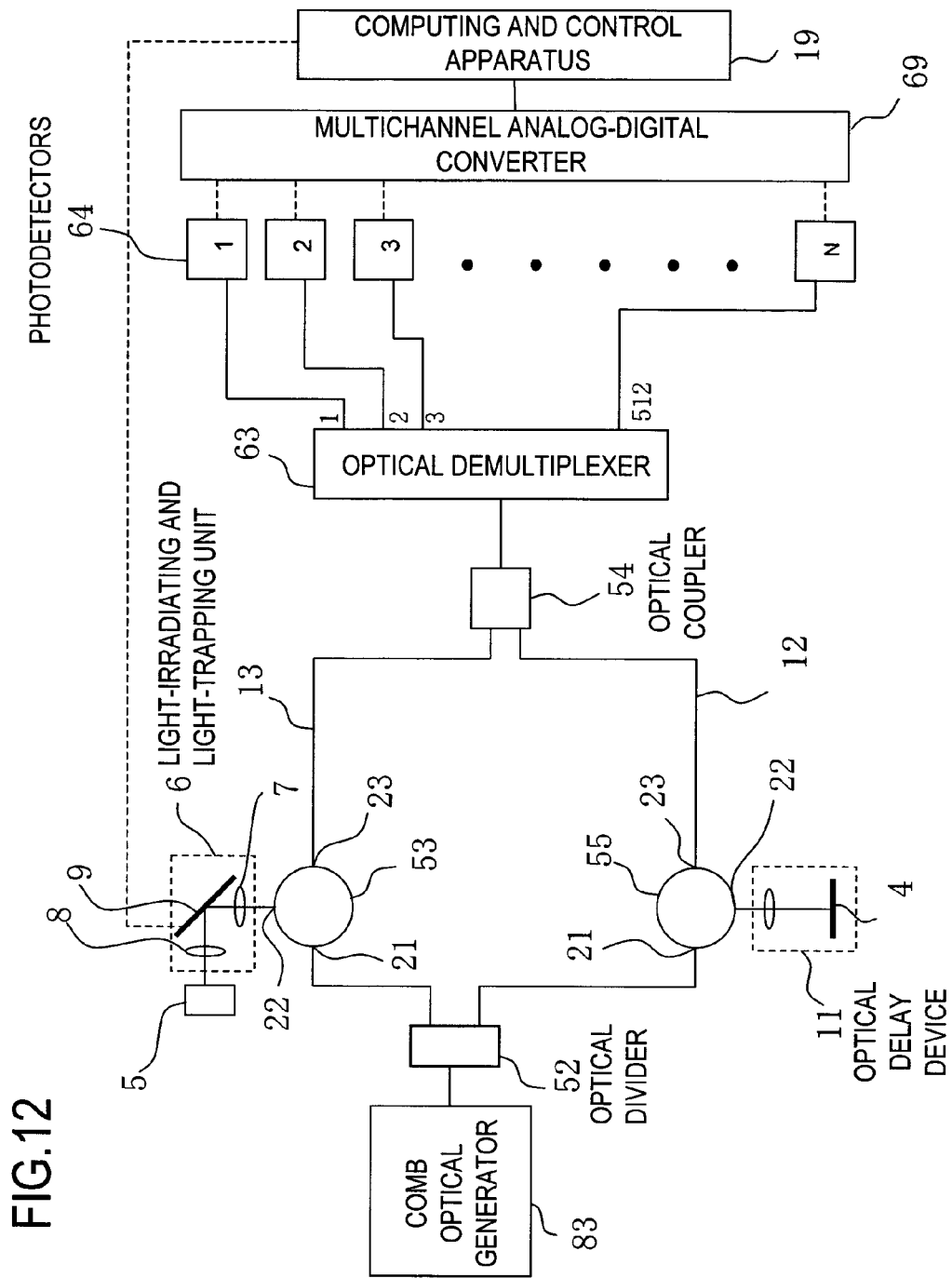
FIG. 12 is a block diagram showing the main parts of an optical coherence tomography apparatus using a comb optical generator.

FIG. 12 is a block diagram of an optical coherence tomography apparatus using a comb optical generator. This apparatus differs from the optical coherence tomography apparatus of the fourth embodiment (FIG. 10) in that no optical filter is used, and a comb optical generator 83 is used as a light source instead of the broadband light generating device 1.

The photo-detecting device 64 may be composed of a semiconductor photo-detector such as a photo diode and an amplifier. However, the photo-detecting device is not limited thereto. For example, a device such as a CCD, which stores a photo-excited photocarrier in a potential well, reads the stored photocarrier after a fixed amount of time, and measures the accumulated charge, may be used.

Figure 13:
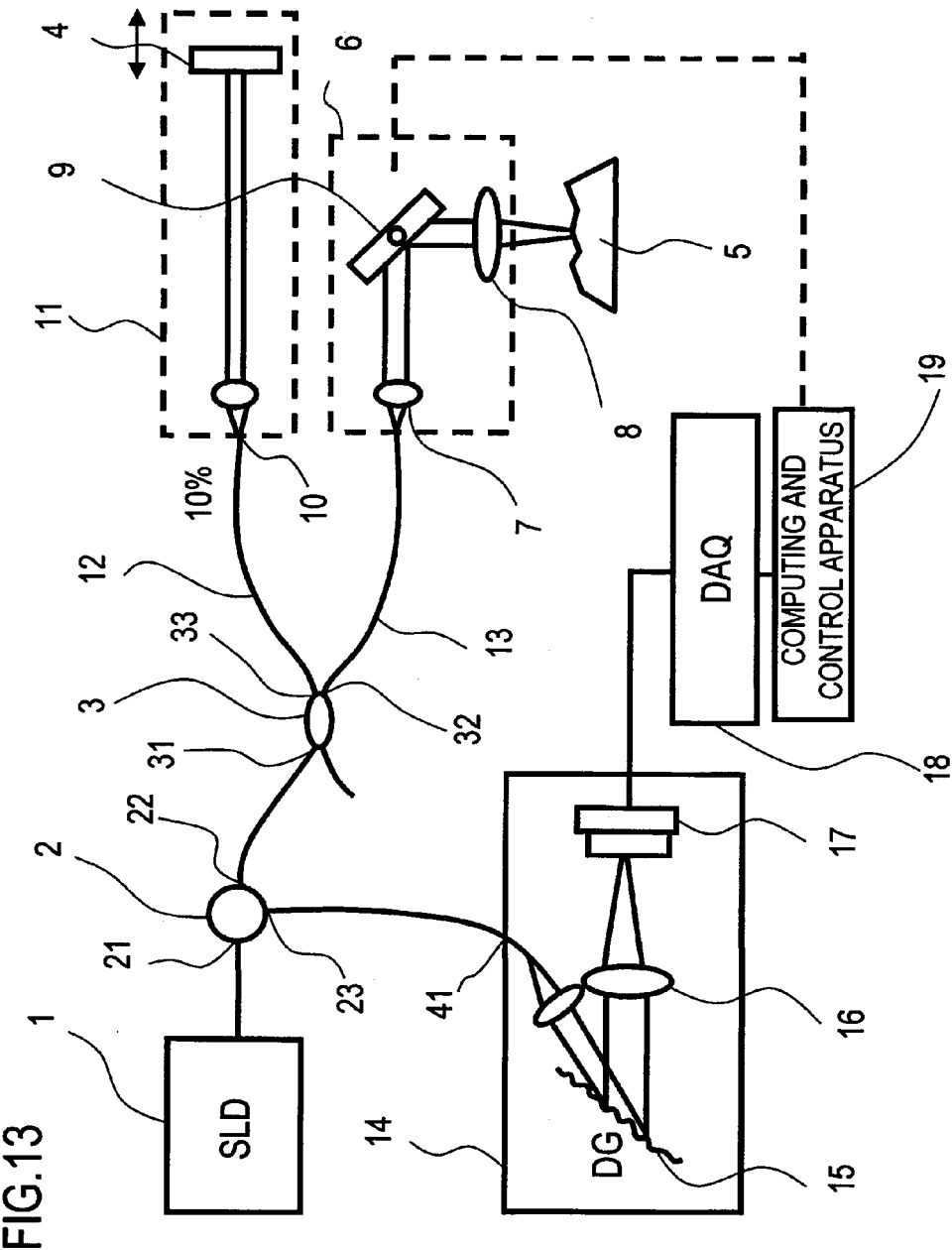
FIG. 13 is a block diagram showing the main parts of a conventional SD-OCT apparatus.
Figure 14:
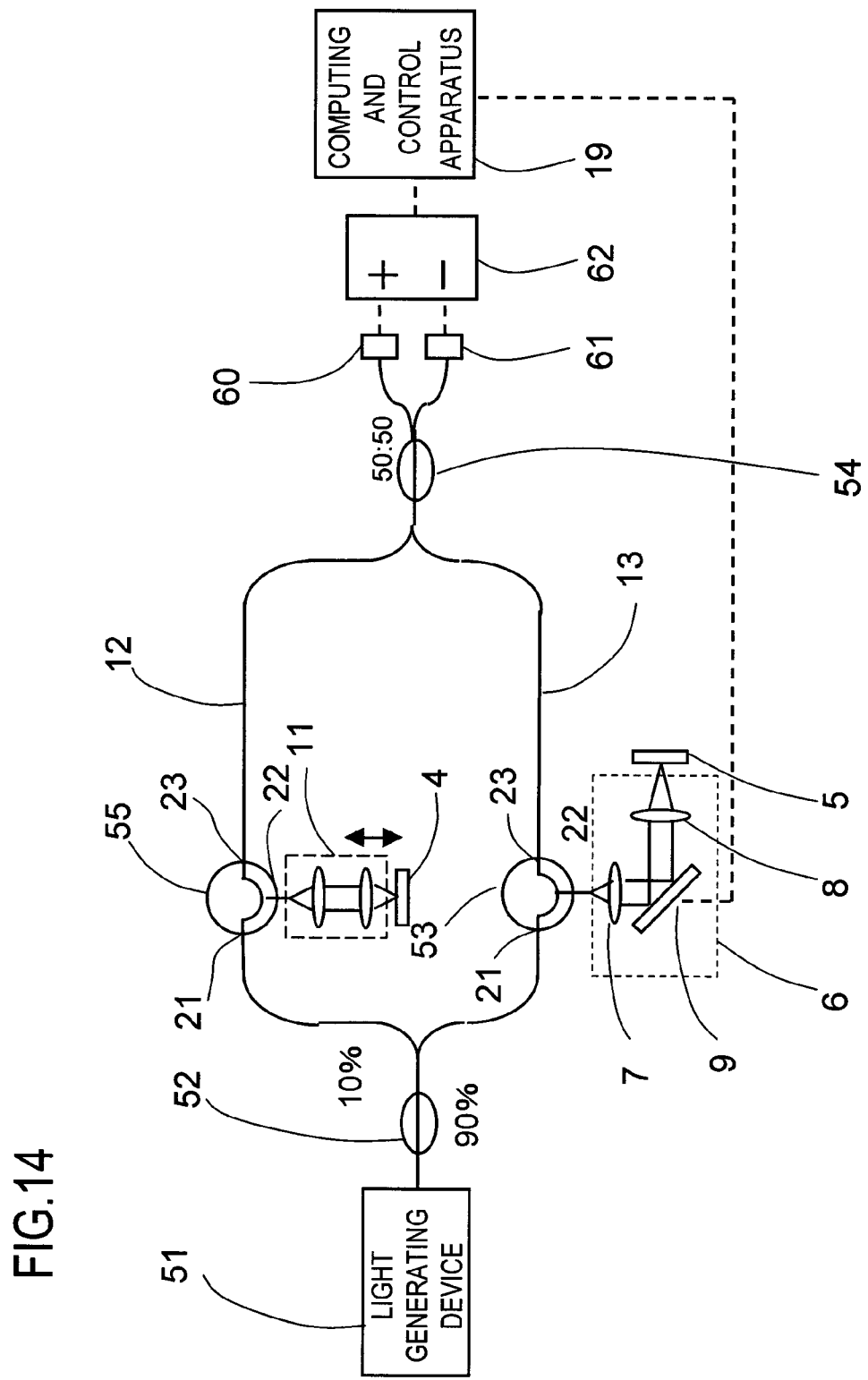
FIG. 14 is a block diagram showing the main parts of a conventional OFDR-OCT apparatus.

Further, the interferometer constituting the OCT apparatus of the above embodiments is a Mach-Zehnder interferometer composed of the first and second couplers 52, 54 and the first and second circulators 53, 55. However, a Michelson interferometer such as that shown in FIG. 13, which is composed of the optical-divider and optical-coupler 3, the reference arm 12, and the sample arm 13, may be used. In other words, the single optical-divider and optical-coupler 3 may function as an optical divider and an optical coupler.

Industrial Applicability

The present invention may be used in the field of medical equipment, and more particularly in the manufacture of diagnostic equipment.

What is claimed is:

1. An optical coherence tomography apparatus comprising:
   a broadband light generating device for outputting light in all wave numbers within a predetermined range;
   an optical divider for dividing output light of said broadband light generating device into measurement light and reference light;
   a light-irradiating and light-trapping unit for irradiating a measurement object with said measurement light and trapping signal light comprising said measurement light reflected or backscattered by said measurement object;
   an optical coupler for combining said signal light and said reference light;
   a first optical demultiplexer for dividing output light of said coupler into a plurality of predetermined wave number sections and outputting divided output light;
   a second optical demultiplexer having a substantially identical structure to said first optical demultiplexer, for dividing another output light of said coupler into said plurality of predetermined wave number sections and outputting divided output light, and
   a group of photo-detecting devices provided in each of said predetermined wave number sections for measuring a difference between a first optical intensity of output light of said first optical demultiplexer and a second optical intensity of output light of said second optical demultiplexer.

2. The optical coherence tomography apparatus according to claim 1, wherein said computing and control apparatus subjects a function expressing a relationship between an intensity of light outputted by said optical coupler and said wave number, which is obtained on the basis of said output of said group of photo-detecting devices, to Fourier transform relative to said wave number, and squares an absolute value thereof.

3. The optical coherence tomography apparatus according to claim 1, wherein said plurality of predetermined wave number sections are separated into equal intervals.

4. The optical coherence tomography apparatus according to claim 1, further comprising a multichannel analog to digital converter for receiving a plurality of analog electric signals outputted by said group of photo-detecting devices simultaneously, and converting said analog signals into digital signals simultaneously; and a computing and control apparatus for specifying, on the basis of an output signal of said multichannel analog to digital converter, a reflection position or backscattering position and a reflection intensity or backscattering intensity of said measurement light relative to an irradiation direction of said measurement light on said measurement object.

5. The optical coherence tomography apparatus according to claim 1, further comprising an optical amplifier for amplifying said signal light.

6. The optical coherence tomography apparatus according to claim 1, wherein a full width at half maximum of a transmission characteristic spectrum of said demultiplexer relative to a wave number in each of said predetermined wave number sections is narrower than a width of each wave number section and greater than 0.2 times said width of each wave number section.

7. The optical coherence tomography apparatus according to claim 1, further comprising an optical filter for shaping said output light of said broadband light generating device such that an optical intensity at each end of each of said predetermined wave number sections is smaller than an optical intensity in the center of each of said predetermined wave number sections, and outputting shaped output light to said optical divider.

8. The optical coherence tomography apparatus according to claim 1, comprising, in place of said broadband light generating device, a comb optical generator for outputting light steadily and simultaneously in each of said predetermined wave number sections such that an optical intensity at each end of each of said predetermined wave number sections is smaller than an optical intensity in the center of each of said predetermined wave number sections.

9. An optical coherence tomography apparatus comprising:

a broadband light generating device for outputting light steadily in all wave numbers within a predetermined range from a first output port;

an optical divider, a first input port of which is optically connected to said first output port of said broadband light generating device, for dividing output light of said broadband light generating device into measurement light and reference light, outputting said measurement light from a second output port, and outputting said reference light from a third output port;

a light-irradiating and light-trapping unit, a second input port of which is optically connected to said second output port of said optical divider, for irradiating a measurement object with said measurement light and trapping signal comprising said measurement light reflected or backscattered by said measurement object, and outputting said signal light from a fourth output port;

an optical delay device, a third input port of which is optically connected to said third output port of said optical divider, for delaying said reference light and outputting delayed output light from a fifth output port;

an optical coupler, a fourth input port of which is optically connected to said fourth output port of said light-irradiating and light-trapping unit, and a fifth input port of which is optically connected to said fifth output port of said optical delay device, for combining said signal light and said reference light and outputting combined output light from a sixth output port and tenth output port;

an first optical demultiplexer, a sixth input port of which is optically connected to said sixth output port of said optical coupler, for dividing output light of said optical coupler into a plurality of predetermined wave number sections and outputting divided output light from a plurality of seventh output ports;

an second optical demultiplexer, a tenth input port of which is optically connected to said tenth output port of said optical coupler, for dividing output light of said optical coupler into a plurality of predetermined wave number sections and outputting divided output light from a plurality of eleventh output ports;

a plurality of photo-detecting devices, seventh input ports and eleventh input ports of which are optically connected individually to said plurality of seventh output ports of said first optical demultiplexer and said plurality of eleventh output ports of said second optical demultiplexer, for measuring a difference between a first optical intensity of output light outputted from each of said seventh output ports and a second optical intensity of output light outputted from each of said eleventh output; and a computing and control apparatus for specifying, on the basis of output of said plurality of photo-detecting devices, a reflection position or backscattering position and a reflection intensity or backscattering intensity of said measurement light relative to an irradiation direction of said measurement light on said measurement object.

10. The optical coherence tomography apparatus according to claim 9, wherein said computing and control apparatus subjects a function expressing a relationship between an intensity of light outputted by said optical coupler and said wave number, which is obtained on the basis of said output of said group of photo-detecting devices, to Fourier transform relative to said wave number, and squares an absolute value thereof.

11. The optical coherence tomography apparatus according to claim 9, wherein said plurality of predetermined wave number sections are a separated into equal intervals.

12. The optical coherence tomography apparatus according to claim 9, further comprising a multichannel analog to digital converter, a plurality of input terminals of which are connected individually to respective first output terminals of said plurality of photo-detecting devices, for receiving analog electric signals outputted by each of said plurality of photo-detecting devices simultaneously, converting said analog signals into digital signals simultaneously, and outputting said digital signals to a second output terminal; and a computing and control apparatus, a second input terminal of which is connected to said second output terminal of said multichannel analog to digital converter, for specifying, on the basis of said digital signals outputted by said multichannel analog to digital converter, a reflection position or backscattering position and a reflection intensity or backscattering intensity of said measurement light relative to an irradiation direction of said measurement light on said measurement object.

13. The optical coherence tomography apparatus according to claim 9, further comprising an optical amplifier, wherein an eighth input port of said optical amplifier is optically connected to said fourth output port of said light-irradiating and light-trapping unit instead of said fourth input port of said optical coupler, an eighth output port of said optical amplifier is optically connected to said fourth input port of said optical coupler instead of said fourth output port of said optical unit, and said optical amplifier amplifies said signal light inputted from said eighth input port, and outputs amplified said signal light to said eighth output port.

14. The optical coherence tomography apparatus according to claim 9, wherein a full width at half maximum of a transmission characteristic spectrum of said demultiplexer relative to a wave number in each of said predetermined wave number sections is narrower than a width of each wave number section and greater than 0.2 times said width of each wave number section.

15. The optical coherence tomography apparatus according to claim 9, further comprising an optical filter, wherein a ninth input port of said optical filter is optically connected to said first output port of said broadband light generating device instead of said first input port of said optical divider, a ninth output port of said optical filter is optically connected to said first input port of said optical divider instead of said first output port of said broadband light generating device, and said optical filter shapes, in each of said predetermined wave number sections, output light of said broadband light generating device, which is inputted from said ninth input port, into light having a full width at half maximum that is narrower than a width of each of said predetermined wave number sections, and then outputs said light to said ninth output port.

16. An optical coherence tomography apparatus comprising:

a comb optical generator for outputting light steadily and simultaneously in each of a plurality of predetermined wave number sections such that an optical intensity at each end of each of said predetermined wave number sections is smaller than an optical intensity in the center of each of said predetermined wave number sections, an optical divider, a first input port of which is optically connected to said first output port of said comb optical generator for dividing output light of said comb optical generator into measurement light and reference light, outputting said measurement light from a second output port, and outputting said reference light from a third output port;

a light-irradiating and light-trapping unit, a second input port of which is optically connected to said second output port of said optical divider, for irradiating a measurement object with said measurement light and trapping signal comprising said measurement light reflected or backscattered by said measurement object, and outputting said signal light from a fourth output port;

an optical delay device, a third input port of which is optically connected to said third output port of said optical divider, for delaying said reference light and outputting delayed output light from a fifth output port;

an optical coupler, a fourth input port of which is optically connected to said fourth output port of said light-irradiating and light-trapping unit, and a fifth input port of which is optically connected to said fifth output port of said optical delay device, for combining said signal light and said reference light and outputting combined output light from a sixth output port and tenth output port;

an first optical demultiplexer, a sixth input port of which is optically connected to said sixth output port of said optical coupler, for dividing output light of said optical coupler into a plurality of predetermined wave number sections and outputting divided output light from a plurality of seventh output ports;

an second optical demultiplexer, a tenth input port of which is optically connected to said tenth output port of said optical coupler, for dividing output light of said optical coupler into a plurality of predetermined wave number sections and outputting divided output light from a plurality of eleventh output ports;

a plurality of photo-detecting devices, seventh input ports and eleventh input ports of which are optically connected individually to said plurality of seventh output ports of said first optical demultiplexer and said plurality of eleventh output ports of said second optical demultiplexer, for measuring a difference between a first optical intensity of output light outputted from each of said seventh output ports and a second optical intensity of output light outputted from each of said eleventh output; and a computing and control apparatus for specifying, on the basis of output of said plurality of photo-detecting devices, a reflection position or backscattering position and a reflection intensity or backscattering intensity of said measurement light relative to an irradiation direction of said measurement light on said measurement object.

* * * * *